United States Patent
Ausserré et al.

(10) Patent No.: US 10,241,311 B2
(45) Date of Patent: Mar. 26, 2019

(54) OPTICAL METHODS FOR OBSERVING SAMPLES AND FOR DETECTING OR METERING CHEMICAL OR BIOLOGICAL SPECIES

(71) Applicants: Centre National de la Recherche Scientifique, Paris (FR); Universite Du Maine, Le Mans (FR); Universite D'Aix-Marseille, Marseilles (FR)

(72) Inventors: Dominique Ausserré, Soulitré (FR); Ludovic Roussille, Marseilles (FR); Myriam Zerrad, Marseilles (FR); Fabien Lemarchand, Cabries (FR); Claude Amra, Marseilles (FR)

(73) Assignees: Centre National de la Recherche Scientifique, Paris (FR); Universite du Maine, Le Mans (FR); Universite d'Aix-Marseille, Marseilles (FR)

( * ) Notice: Subject to any disclaimer, the term of this patent is extended or adjusted under 35 U.S.C. 154(b) by 954 days.

(21) Appl. No.: 14/417,397

(22) PCT Filed: Jul. 26, 2013

(86) PCT No.: PCT/IB2013/056153
§ 371 (c)(1),
(2) Date: Jan. 26, 2015

(87) PCT Pub. No.: WO2014/016813
PCT Pub. Date: Jan. 30, 2014

(65) Prior Publication Data
US 2015/0185457 A1    Jul. 2, 2015

(30) Foreign Application Priority Data

Jul. 26, 2012    (FR) ...................... 12 57279

(51) Int. Cl.
*G01N 33/552*    (2006.01)
*G02B 21/06*    (2006.01)
(Continued)

(52) U.S. Cl.
CPC ............. *G02B 21/06* (2013.01); *G01N 21/03* (2013.01); *G01N 21/359* (2013.01); *G01N 21/59* (2013.01);
(Continued)

(58) Field of Classification Search
None
See application file for complete search history.

(56) References Cited

U.S. PATENT DOCUMENTS 7,307,726 B2 *  12/2007  Ausserre ............ G01B 11/0616
                                                        356/369
7,652,762 B2 *   1/2010  Ausserre ................. G01J 4/00
                                                        356/244

(Continued)

FOREIGN PATENT DOCUMENTS

EP     1 496 363 A1    1/2005
FR     2 818 376 A1    6/2002
(Continued)

OTHER PUBLICATIONS

International Search Report and Written Opinion for Application No. PCT/IB2013/056153 dated Nov. 5, 2013.

(Continued)

*Primary Examiner* — Christopher L Chin
(74) *Attorney, Agent, or Firm* — Alston & Bird LLP

(57) ABSTRACT

The invention relates to a method for observing a sample under optical microscopy, in incoherent, unpolarised light, using a sample substrate including a contrast-amplifying layer having a complex index of refraction. The invention also relates to a method for detecting or metering at least one (Continued)

chemical or biological species using such a sample substrate.

12 Claims, 32 Drawing Sheets

(51) Int. Cl.
| | |
|---|---|
| *G01N 33/543* | (2006.01) |
| *G01N 33/551* | (2006.01) |
| *G01N 21/359* | (2014.01) |
| *G01N 21/59* | (2006.01) |
| *G01N 21/03* | (2006.01) |
| *G01N 21/84* | (2006.01) |
| *G02B 21/33* | (2006.01) |
| *G02B 21/34* | (2006.01) |

(52) U.S. Cl.
CPC ... *G01N 21/8422* (2013.01); *G01N 33/54373* (2013.01); *G01N 33/551* (2013.01); *G02B 21/33* (2013.01); *G02B 21/34* (2013.01)

(56) References Cited

U.S. PATENT DOCUMENTS

| | | | | |
|---|---|---|---|---|
| 8,088,615 | B2* | 1/2012 | Ausserre | G01N 21/21 |
| | | | | 356/369 |
| 2006/0103933 | A1* | 5/2006 | Ausserre | G01J 4/00 |
| | | | | 359/487.05 |
| 2007/0188755 | A1* | 8/2007 | Ausserre | G01B 11/0616 |
| | | | | 356/369 |
| 2010/0062422 | A1* | 3/2010 | Ausserre | G01N 21/21 |
| | | | | 435/6.12 |
| 2011/0194106 | A1 | 8/2011 | Murakami et al. | |
| 2016/0282611 | A1* | 9/2016 | Ausserre | G02B 1/02 |
| 2016/0299328 | A1* | 10/2016 | Ausserre | G02B 1/11 |

FOREIGN PATENT DOCUMENTS

| | | |
|---|---|---|
| FR | 2 872 910 A1 | 1/2006 |
| JP | H 06-265336 A | 9/1994 |
| JP | 2005-180921 A | 7/2005 |
| JP | 2008-506098 A | 2/2008 |
| WO | WO 02/50513 A1 | 6/2002 |
| WO | WO 2004/001399 A1 | 12/2003 |
| WO | WO 2009/112431 A1 | 9/2009 |

OTHER PUBLICATIONS

Ausserre, D. et al., *Surface Enhanced Ellipsometric Contrast (SEEC) Basic Theory and λ/4 Mutilayered Solutions*, Optics Express, vol. 15, No. 13, (Jun. 25, 2007).

Meyer, S. A. et al., *Combining Surface Plasmon Resonance (SPR) Spectroscopy With Surface-Enhanced Raman Scattering (SERS)*, Anal. Chem. (2011) 83, 2337-2344.

Campbell, C.T. et al., *SPR Microscopy and Its Applications to High-Throughput Analyses of Biomolectular Binding Events and Their Kinetics*, Biomaterials 28 (2007) 2380-2392.

Stewart, M. E. et al., *Nanostructured Plasmonic Sensors*, Chem. Rev. (2008) 108, 494-521.

Wang, G. et al., *Optical Parameters and Absorption Studies of Azo Dye-Doped Polymer Thin Films on Silicon*, Materials Letters 43 (2000) 6-10.

* cited by examiner

OPTICAL METHODS FOR OBSERVING SAMPLES AND FOR DETECTING OR METERING CHEMICAL OR BIOLOGICAL SPECIES

FIELD

The invention relates to an optical process for observing samples, and also to an optical process for detecting or quantitatively determining chemical or biological species. These processes are based on the same newly discovered principle.

The invention is capable of being applied to various technical fields, such as biology (detection of biomolecules or microorganisms, observation of cell cultures), nanotechnologies (visualization of nano-objects, such as nanotubes), microelectronics, materials science, etc. In some of these fields, it can constitute an alternative to conventional detection techniques based on surface plasmons, such as the SPR (Surface Plasmon Resonance), LSPR (localized SPR) and SERS (Surface-Enhanced Raman Spectroscopy) techniques. For a description of these conventional techniques, reference may be made to the article by M. E. Stewart et al. "Nanostructured Plasmonic Sensors", Chem. Rev. 2008, 108, 494-521 and to the article by S. A. Meyer et al. "Combining Surface Plasmon Resonance (SPR) Spectroscopy with Surface-Enhanced Raman Scattering (SERS)", Anal. Chem. 2011, 83, 2337-2344.

BACKGROUND

A limit of these techniques consists of the fact that it is difficult to obtain a high spatial resolution that would be useful, for example, for increasing the density of a biochip. This is because these techniques use a functionalized metallic layer, which must be illuminated with a collimated, and therefore not focused, light beam, otherwise there is a considerable loss of contrast (see the abovementioned article by S. A. Meyer et al.). It is not therefore possible to illuminate and observe a conventional plasmon sensor under optical microscopy. The other plasmon imaging techniques used with a parallel illuminating beam have, in all cases, a resolution limited to a few tens of microns; see, for example, Charles T. Campbell, Gibum Kim "SPR microscopy and its applications to high-throughput analyses of biomolecular binding events and their kinetics" Biomaterials 28 (2007) 2380-2392.

Document WO 2004/001399 and the article by D. Ausserré and M. P. Valignat "Surface enhanced ellipsometric contrast (SEEC) basic theory and $\lambda/4$ multilayered solutions", Optics Express, Vol. 15, No. 13, Jun. 25, 2007, describe a high-contrast optical microscopy technique, known as "surface-enhanced ellipsometric contrast", or SEEC, which is illustrated in FIG. 1. In accordance with this technique, a sample to be observed EO is deposited on a contrast-amplifying support SAC', comprising a substrate SR, which is generally a reflecting substrate, and an antireflection layer or multilayer structure CA. The assembly made up of the sample and its support is illuminated by a spatially incoherent light beam F, linearly polarized by means of a polarizer P. The beam F may be annular; in any event, it is focused on the support-sample assembly by means of an objective LO, and its propagation axis is perpendicular to the surface of said support. In the case of an annular beam F, the light rays form, with the normal to the support, an angle of incidence of between $\theta_{min}$ and $\theta_{max}$; if the beam is not annular, $\theta_{min} \rightarrow 0°$. The observation is made through a polarization analyzer A, generally oriented in such a way that its polarization axis is perpendicular to the direction of polarization of the beam F (it is then said that the polarizer P and the analyzer A are crossed); advantageously, the objective LO is also used for the observation. Thus, said objective and also the polarizer and the analyzer form a polarizing microscope.

The antireflection layer or multilayer structure CA is proportioned so as to minimize—ideally to cancel out—the light intensity which, reflected by the support SAC', passes through the analyzer A. The object, which is generally transparent, disrupts the extinction condition, and therefore appears as a luminous form on a black background.

Strictly speaking, the extinction condition is satisfied for a single angle of incidence $\theta_0$, which would correspond to an annular illumination with $\theta_{min} = \theta_{max} = \theta_0$; however, obviously, under these conditions, the light intensity tends toward zero. More realistically, the interval $\theta_{max}\theta_{min}$ may be chosen to be about 5°. As a variant, the abovementioned documents indicate that it is possible to have recourse to a "conical" illumination (i.e. a nonannular illumination, characterized by $\theta_{min}=0°$), with $\theta_{max}$ possibly reaching 20° or even 30°. In this case, the support SAC' is proportioned on the basis of an average angle of incidence.

Under these conditions, the choice of the illumination conditions is a compromise, which cannot be entirely satisfactory. This is because:
- an annular illumination is difficult to implement and involves a light intensity which is all the weaker the smaller the interval $\theta_{max} - \theta_{min}$;
- a strongly converging conical illumination, with $\theta_{max}$ of about 20° or more, results in a weak contrast since the extinction is actually obtained only at a single angle of incidence; and
- a weakly converging conical illumination implies a small aperture of the objective, thereby limiting the spatial resolution with which the sample is observed.

Like the SPR technique, the SEEC method can be applied to biological or biochemical analyses. For example, the support SAC' can constitute the bottom of a Petri dish, in which case the observation must generally be made by immersion in a culture medium, which is sometimes difficult.

Document WO 02/50513 describes the application of the SEEC technique to the performing of ellipsometric measurements with spatial resolution, and also to the fabrication of biological sensors. In this case also, it is difficult to obtain both a high spatial resolution and a satisfactory contrast; moreover, the observation is sometimes difficult, in particular with regard to the applications to biology or to biochemistry.

SUMMARY

The invention aims to remedy the abovementioned prior art drawbacks. To do this, it is based on an effect which has been newly discovered by the present inventors. Indeed, the latter have realized that, when a thin object (typically a layer of nanometric thickness) is deposited on a support comprising a transparent substrate and a metallic or more generally absorbent coating, and then it is observed under inverted geometry microscopy (i.e. with illumination and observation through the substrate), this produces—for certain values of the thickness of the coating—a relatively high contrast virtually independent of the numerical aperture of the microscope in a wide range of variation of said aperture. Just as surprisingly, this effect is noted both under polarized light (observation through a polarizer and an analyzer which are crossed) and under unpolarized light. Although the use of polarized light allows, under certain conditions, an increase in contrast, the use of unpolarized light avoids the loss of light caused by the polarizer and the analyzer, simplifies the implementation of the process and makes it possible to obtain images which are more homogeneous.

A subject of the invention is therefore a process for observing a sample, comprising the steps consisting in:
a) providing a sample support comprising a transparent substrate on which is deposited at least one layer, termed contrast-amplifying layer, having a complex refractive index with an imaginary part κ greater than or equal to 0.001, and preferentially greater than or equal to 0.011;
b) placing the sample to be observed on said support, on the side of said contrast-amplifying layer;
c) directing onto said sample, through said substrate, a polarized or unpolarized, spatially incoherent light beam, focused so as to form an illumination cone having an aperture half-angle θ greater than or equal to 20 degrees (°); and
d) observing said sample through an objective and said substrate;
said contrast-amplifying layer being proportioned in such a way that said sample is observed with a higher contrast than in the absence of said support.

An observation under polarized light, for example between a polarizer and an analyzer which are crossed, is also possible.

The observation can be carried out with the naked eye or with an image sensor such as a CCD matrix. If only the light intensity reflected by a portion of the sample must be measured (for example, in applications of biochip type), the observation can be carried out by means of a photodetector such as a photomultiplier or a photodiode.

According to various embodiments of such a process:
Said contrast-amplifying layer may be metallic. Other absorbent materials which may be suitable for producing a contrast-amplifying layer according to the invention are semiconductors, metal oxides, alloys of metals and/or of semiconductors, dielectrics (in particular photosensitive polymers or resins) loaded with dyes, polyelectrolytes (because of the metal counterions associated with the charges), fluorescent substances, nanoparticle films, composite materials formed from a mixture of these constituents, in particular dielectrics loaded with absorbent nanoparticles. The use of a dielectric layer loaded with dye or with nanoparticles constitutes a particularly advantageous option since it makes it possible to adjust κ at fixed n by adjusting the concentration of the dye or of the nanoparticles, respectively. In this respect, see Guangbin Wang, Fuxi Gan "Optical parameters and absorption studies of azo dye-doped polymer thin films on silicon" Materials Letters 43 2000, 6-10. Another interesting case consists of scattering media which have a significant κ which is adjustable via the size and the density of the scattering centers, owing to the losses due to scattering.

The aperture half-angle of said illumination cone can be between 20° and 75°, preferably between 30° and 70°, and more preferably between 40° and 65°, the axis of said cone being perpendicular to said substrate.

Said objective can be used both for illuminating and for observing said sample.

Said contrast-amplifying layer and said sample can be immersed in water or in an aqueous solution.

Said contrast-amplifying layer may have a thickness gradient.

The thickness or a local thickness of said contrast-amplifying layer can be determined so as to optimize the contrast, for at least one wavelength of the illumination, integrated on said illumination cone, with which a reference sample consisting of a variation in thickness of said contrast-amplifying layer would be observed.

The process may comprise a preliminary step of proportioning said contrast-amplifying layer, comprising:
calculating (typically by means of a computer) an area representing the contrast with which said reference sample would be observed as a function of the thickness of said layer, normalized with respect to an illumination wavelength, and the aperture half-angle θ of the illumination beam;
identifying a crest or thalweg of said area, having an orientation approximately parallel to the axis representing said aperture half-angle θ;
identifying a value, or range of values, of thickness of said layer corresponding to said crest or thalweg;
the thickness or a local thickness of said contrast-amplifying layer being chosen equal to the value, or within the value range, thus identified.

It is recalled that a thalweg is defined as the bottom line of a valley.

Said sample support may have, above said contrast-amplifying layer, a functionalization layer capable of binding at least one chemical or biological species, the process also comprising a step of bringing said functionalization layer into contact with a solution of said chemical or biological species to be bound, as a result of which said chemical or biological species forms a layer above said functionalization layer, constituting the sample to be observed. The contrast is better if said chemical or biological species is absorbent, having a complex refractive index with an imaginary part κ greater than or equal to 0.0001, or scattering. The functionalization layer may be in the form of a plurality of spots capable of binding different chemical or biological species; in this case, it is preferable for said contrast layer to be deposited only in positions corresponding to said spots and/or for said support to comprise, outside said spots, a passivation layer which prevents the binding of any chemical or biological species contained in said solution.

Another subject of the invention is a process for detecting or quantitatively determining at least one chemical or biological species, comprising the steps consisting in:
a) providing a transparent substrate on which is deposited at least one functionalization layer capable of binding at least one chemical or biological species;
b) placing said functionalization layer in contact with at least one solution containing a chemical or biological species labeled with metal nanoparticles or an absorbent label (i.e. optically absorbent for at least one illumination wavelength), said species being capable of binding to said functionalization layer, either directly, or by means of one or more other chemical or biological species, as a result of which said particles form a continuous or discontinuous, absorbent or scattering, metallic layer;
c) directing onto the assembly made up of at least said functionalization and metallic, absorbent or scattering, layers, through said substrate, a spatially incoherent, preferably unpolarized, light beam focused so as to form an illumination cone having an aperture half-angle θ greater than or equal to 20°; and d) observing said assembly through an objective and through said substrate, wherein said light beam is not polarized.

The absorbent or scattering metallic layer acts here both as a contrast-amplifying layer and as a sample; its presence or its absence, and also its variations in thickness, or effective thickness, are visualized with a relatively high contrast, thereby making it possible to detect the presence of said chemical or biological species, and/or to measure the concentration thereof (quantitative determination).

An observation under polarized light, for example between a polarizer and an analyzer which are crossed, is also possible, and the proportioning of the layer is carried out in the same way, but generally results in a layer of different thickness, and with different conditions regarding the refractive indices. Likewise, it is possible not to focus the illumination light beam and/or not to carry out the observation through an objective, but this results in a loss of spatial resolution.

According to a first embodiment of such a process, during step b), said functionalization layer is placed in contact with a solution containing the chemical or biological species to be detected or quantitatively determined, labeled with metal nanoparticles or an absorbent or scattering label, said species being capable of binding to said functionalization layer so as to form said continuous or discontinuous metallic layer.

According to a second embodiment of such a process, said step b) comprises the substeps consisting in:

b1) placing said functionalization layer in contact with a first solution containing the chemical or biological species to be detected or quantitatively determined, so as to form an "intermediate" layer; and b2) placing said intermediate layer in contact with a second solution, containing an "auxiliary" chemical or biological species, labeled with metal nanoparticles or an absorbent label and capable of binding to said intermediate layer so as to form said continuous or discontinuous, absorbent or scattering, metallic layer.

According to a third embodiment of such a process, said step b) comprises the substeps consisting in:

b1) placing said functionalization layer in contact with a first solution containing a chemical or biological species, termed intermediate species, labeled with metal nanoparticles or an absorbent or scattering label and capable of binding to said functionalization layer so as to form said continuous or discontinuous, metallic or absorbent layer; and b2) placing said functionalization layer and said metallic or absorbent layer in contact with a second solution containing said chemical or biological species to be detected or quantitatively determined, which has an affinity with said functionalization layer greater than that of said intermediate species, as a result of which said intermediate species is displaced and said metallic, absorbent or scattering layer is at least partially eliminated.

According to a fourth embodiment of such a process, during said step b), said functionalization layer is placed in contact with a solution containing the chemical or biological species to be quantitatively determined, and also said competing chemical or biological species, one of the two species being labeled with metal nanoparticles or an absorbent or scattering label, as a result of which a continuous or discontinuous, metallic or absorbent layer is obtained, the effective refractive index and the effective thickness of which depend on the ratio between the concentration of said competing chemical or biological species and that of said chemical or biological species to be quantitatively determined.

The aperture half-angle of said illumination cone may advantageously be between 20° and 75° and preferably between 30° and 70° and preferably between 40° and 65°, the axis of said cone being perpendicular to said substrate.

The same objective can be used for illuminating and for observing said sample.

Advantageously, a "contrast-amplifying" layer, having a complex refractive index with an imaginary part κ greater than or equal to 0.001 and preferentially greater than or equal to 0.01, may be interposed between said substrate and said functionalization layer.

Said functionalization layer may be in the form of a plurality of spots placed on the surface of said substrate and capable of binding different chemical or biological species (biochip). The observation through an objective makes it possible to exploit a particularly dense biochip. Advantageously, said support may comprise, outside said spots, a passivation layer which prevents the binding of any chemical or biological species contained in said solution.

Preferably, said spatially incoherent light beam is not polarized.

BRIEF DESCRIPTION OF THE DRAWINGS

Other characteristics, details and advantages of the invention will emerge on reading the description provided with reference to the appended drawings given by way of example and which represent, respectively:

FIGS. 4-1 to 4-56 show areas expressing the contrast with which a reference sample is observed as a function of the half-angle of the illumination cone, θ, and of the thickness of the contrast-amplifying layer, normalized with respect to the wavelength, e/λ (in the case of a polychromatic illumination, λ is the average wavelength); each figure corresponds to a different material, characterized by a (n,κ) pair;

DETAILED DESCRIPTION

A conventional antireflecting layer has a thickness equal to $\lambda/4n_1$ ($\lambda$ being the wavelength of the light in a vacuum and $n_1$ the refractive index of the layer, supposedly real), and a refractive index given by:

$$n_1 = \sqrt{n_0 n_2} \quad (1)$$

where $n_2$ is the refractive index of the substrate on which the layer is deposited and $n_0$ the refractive index of the medium which is above the layer (for example, air). The indices $n_0$ and $n_2$ are considered to be real, just like $n_1$.

A substrate on which an antireflecting layer is deposited can be used as a contrast-amplifying support, but it proves to be poorly suited to the observation of objects of low contrast under an optical microscope. The SEEC technique modifies the reflection suppression condition so as to adapt it to the case of an observation under polarized light and through a polarization analyzer, but it makes it possible to overcome this limitation only very partially, as has been discussed above.

In order to obtain a satisfactory contrast amplification in a very wide range of angles of incidence of the illuminating light (and therefore, in particular, under a microscope with a large numerical aperture), the present invention proposes exploiting an additional degree of freedom: the imaginary part $\kappa$ of the refractive index, which entails the use of an absorbent or metallic layer.

Figure 2:
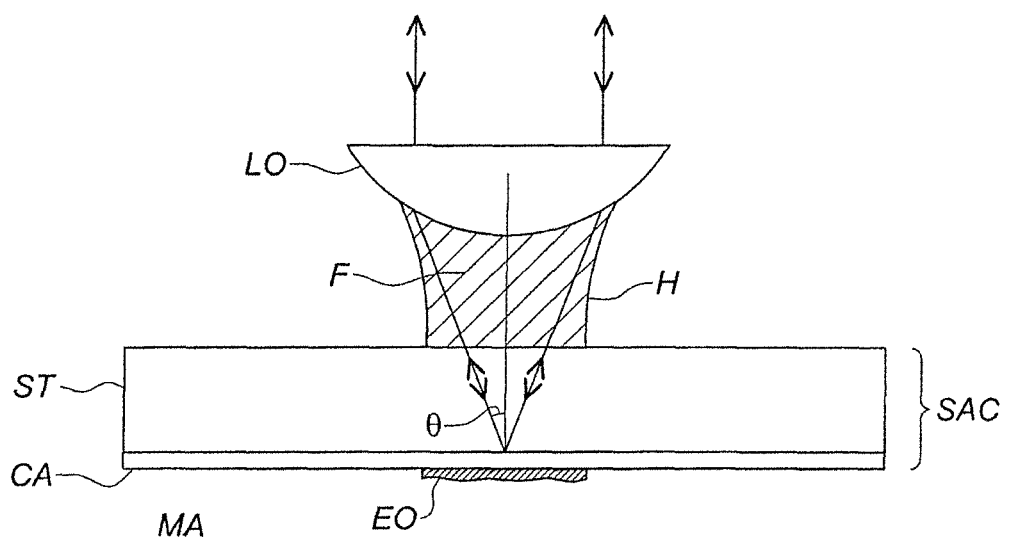
FIG. 2 shows an optical assembly for implementing a process for observing a sample according to one embodiment of the invention.

The case, illustrated in FIG. 2, of a thin layer CA having a refractive index $\tilde{n}_1 = n_1 - j\kappa_1$ of which the imaginary component is not insignificant, for example greater than 0.001 (the convention according to which positive $\kappa_1$ corresponds to an absorption is followed), deposited on a transparent substrate ST with a real index $n_2$, for example made of glass, and immersed in an ambient medium MA with a real index $n_0$, for example air or water, is considered. By way of nonlimiting example, the case of a metallic layer will be considered. A reference sample EO, made up of a small thickness (nanometric) of a transparent material (real index), is placed on the metallic layer. The assembly made up of the support SAC (substrate and metallic layer) and the sample is illuminated and observed through an objective LO with a numerical aperture $n_0 \cdot \sin\theta$ and through the substrate. A drop of oil H can optionally be used to minimize the parasitic reflections between the objective and the ambient medium and between the ambient medium and the substrate. Alternatively, the front face of the substrate may be covered with an antireflection treatment covering the illumination spectrum or the useful part of the illumination spectrum.

As in the case of a conventional antireflecting substrate ($\kappa_1 = 0$), the contrast with which the sample is viewed depends greatly on the complex index and on the thickness of the layer, and more specifically has a marked extremum as a function of the thickness. This extremum itself takes an extremal value and abruptly changes sign when the real and imaginary parts of the complex index $\tilde{n}_1 = n_1 - j\kappa_1$ of the layer satisfy the relationship:

$$n_1^2 - \kappa_1^2 = n_0 n_2 \quad (2)$$

The relationship (2) can be considered to be a generalization of the relationship (1) in the case of a layer having a complex refractive index.

When $n_0$ and $n_2$ are fixed, the reflectivity of the surface depends only on the angle $\theta$, on $\lambda$ (wavelength), on $n_1$ and on $\kappa_1$. Since it is expressed as a function of Fresnel's coefficients (which do not explicitly involve the wavelength $\lambda$, but only the indices of the media and the angles) and of the thickness $e_1$ of the layer (which is involved only through the ratio), it is possible to calculate the contrast of an achromatic reference object as a function of $n_1$, $\kappa_1$ and, this calculation being valid for all metals and all wavelengths. It is thus possible to adjust the operating point by changing metal (or more generally material with a complex refractive index), by changing layer thickness, or by changing wavelength.

Figure 3:
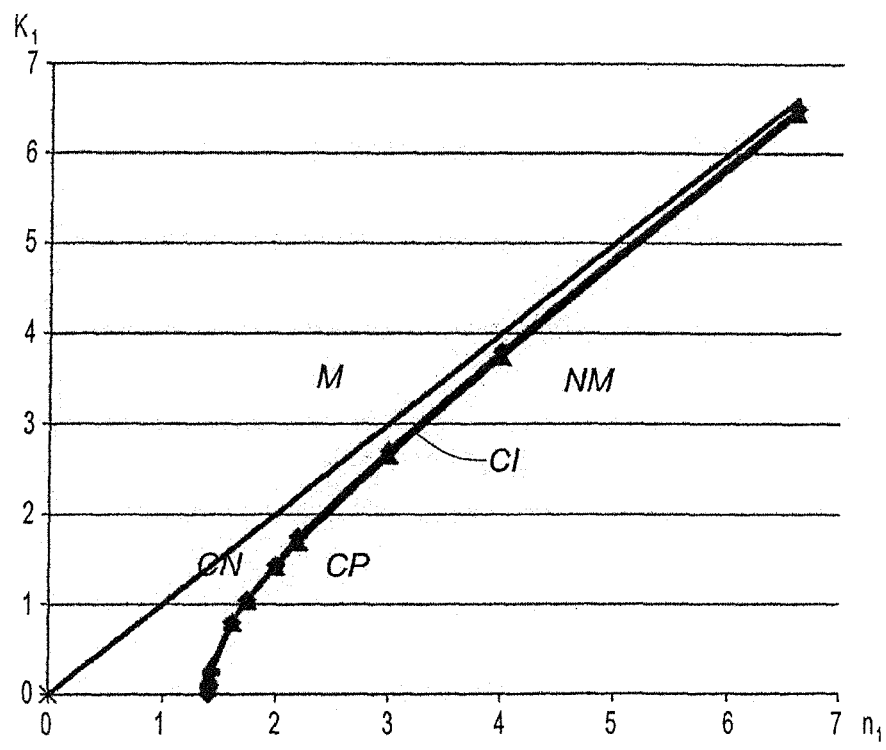
FIG. 3 illustrates the contrast inversion line in the plane n-κ of a sample support suitable for implementing the invention (n being the real part of the refractive index of the contrast-amplifying layer and κ its imaginary part)

In FIG. 3, the straight line with a unitary slope corresponds to the condition $\kappa_1 = n_1$. The region above the straight line, marked M, corresponds to the metallic materials, while the region below, marked NM, corresponds to the nonmetallic materials. The curve IC is defined by the equation (2) and corresponds to the contrast inversion condition. Above this curve (region CN), the contrast is negative, which means that the sample appears dark on a light background; below (region CP), the contrast is positive, which means that the sample appears light on a dark background. The curve has been calculated for $n_0 = 1.514$ and $n_2 = 1.33$.

Figure 1:
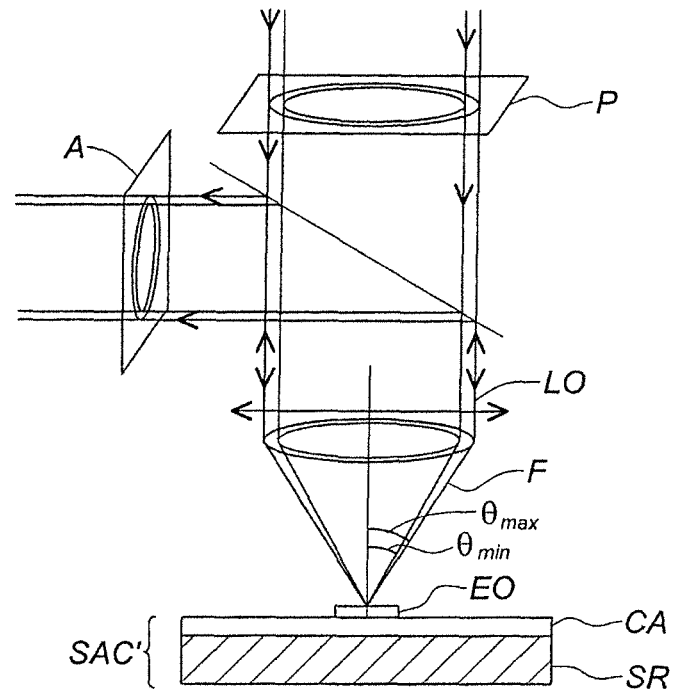
FIG. 1, described above, illustrates the SEEC technique known from the prior art.
Figure 5:
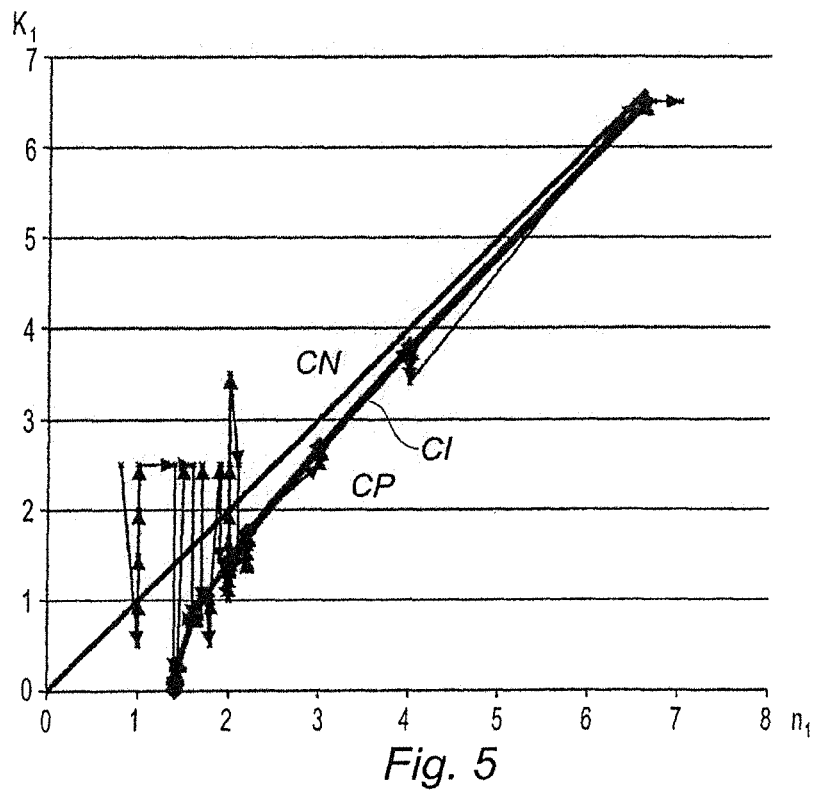
FIG. 5 locates the materials of FIGS. 4-1 to 4-56 in the plane n-κ.
Figures 1, 4:
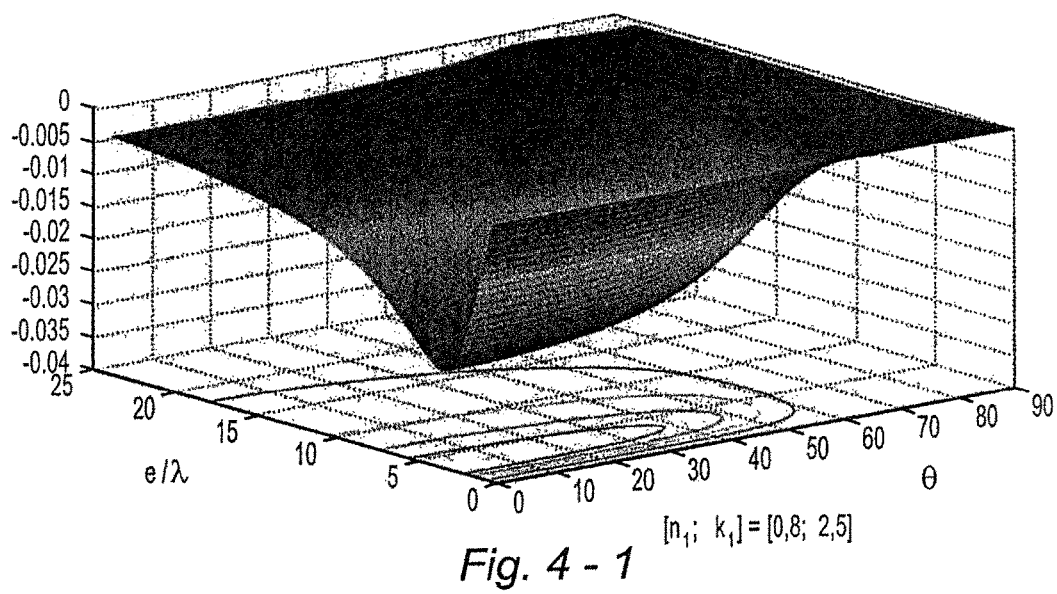
Figures 2, 4:
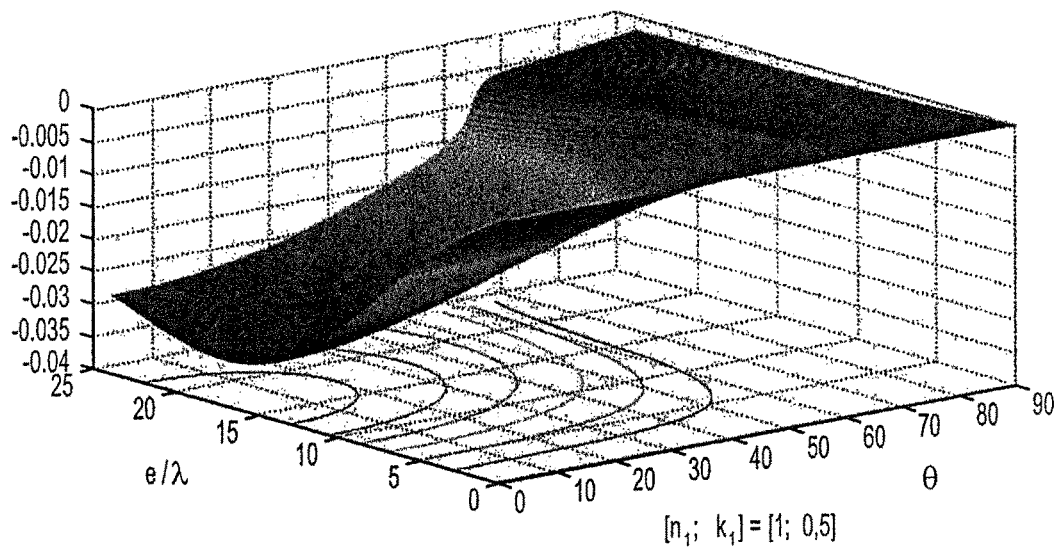
Figures 3, 4:
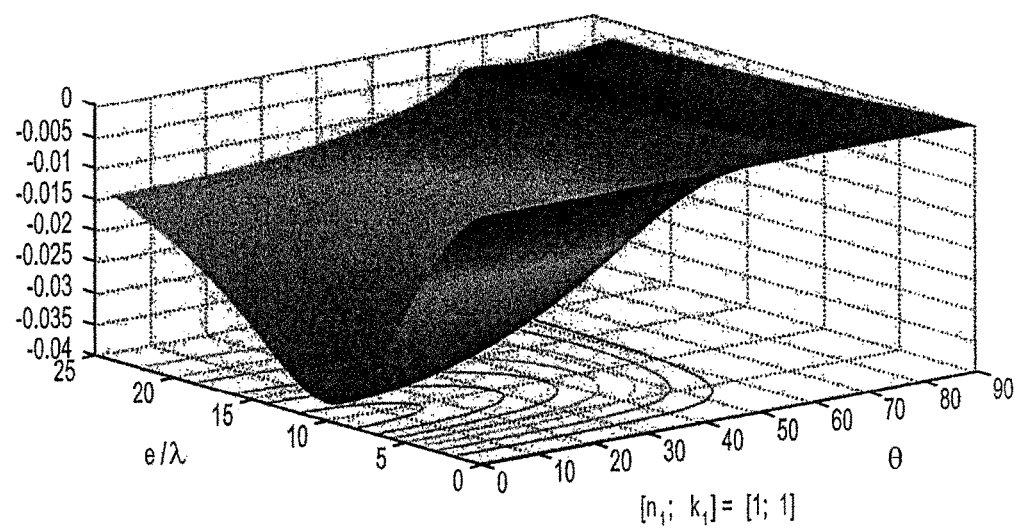
Figure 4:
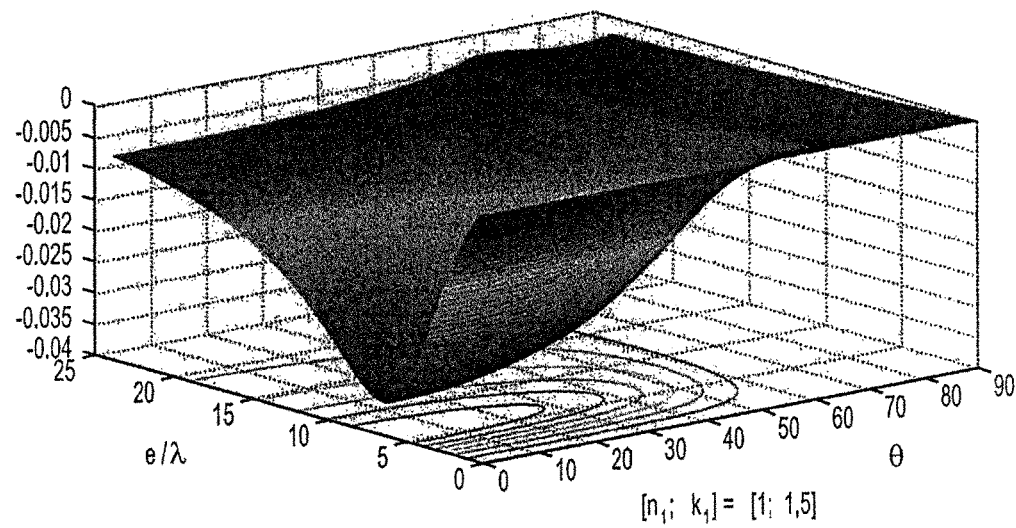
Figures 4, 5:
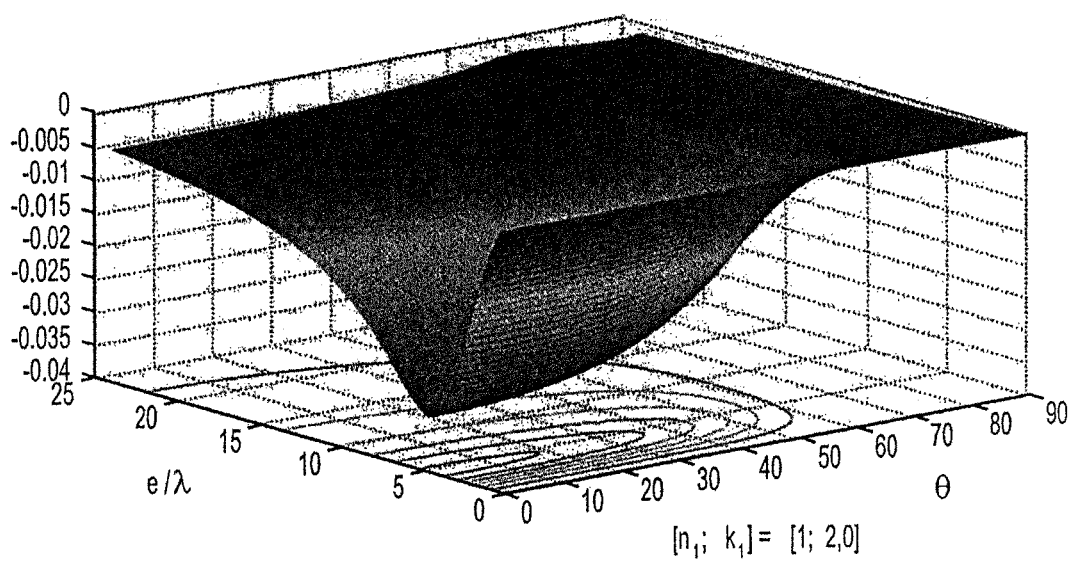
Figures 4, 5, 6:
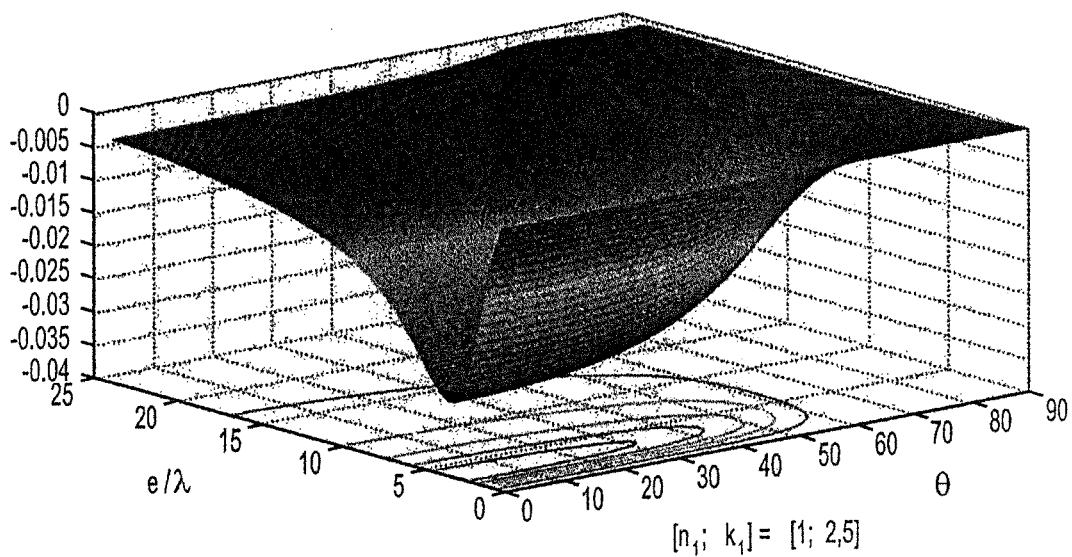

It is advantageous to plot the areas (FIGS. 4-1 to 4-56) expressing the contrast with which the reference sample is observed as a function of $\theta$ and of $e/\lambda$ for a plurality of pairs ($n_1$, $\kappa_1$) located in proximity to the curve IC, on either side of the latter, as illustrated in FIG. 5. It can be observed in FIGS. 4-1 to 4-56 that most of these areas exhibit either valleys (in the case of negative contrast) or "ridges" (in the case of positive contrast), substantially aligned according to the representative axis of the angle $\theta$. This means that, for a defined value of the normalized thickness $e/\lambda$ (corresponding to the crest of the ridge and to the bottom of the valley, i.e. to the thalweg), termed critical thickness $(e/\lambda)_c$, the contrast has a maximum value which is not dependent on, or is only slightly dependent on, $\theta$ as long as this angle is maintained in a defined range (usually extending from 0° to 40-50°). This means that, for said critical value of the normalized thickness $(e/\lambda)_c$, the illumination and the observation through an objective do not lead to a marked loss of contrast as for example in the SEEC technique. The value $e/\lambda$ maximizes (in absolute value) the integrated contrast on all the angles of incidence contained in the illumination cone. The contrast values can vary, by more than 10% to a few per thousand, which is still exploitable. In the case of FIGS. 4-1 to 4-56, $n_0 = 1.514$ and $n_2 = 1.33$ were chosen, which corresponds to a glass substrate and to an observation by immersion in water. Generally, the critical thickness increases with the optical index of the substrate.

Empirically, the relationship which links the critical thickness $(e/\lambda)_c$ to the imaginary part of the index of the contrast-amplifying layer can be written in the form:

$$(e/\lambda)_c = C/\kappa \quad (3)$$

where C is a constant which, in the example considered here, is 0.01. There still remains a parameter of free proportioning, $n_1$, which can be used to choose the best compromise between acceptable numerical aperture (length of the crest or of the thalweg) and contrast (height of the crest or depth of the valley) for a given application. Indeed, the closer the ($n_1$, $\kappa_1$) pair is to the contrast inversion line, the higher the contrast will be at low aperture (or for a predetermined angle of incidence), but the more rapidly it will become unconfined with the numerical aperture of the objective.

A crest or thalweg is also observed in the case of observation under polarized light (between a polarizer and an analyzer which are crossed, or in any event forming an angle between them), and in particular for $\kappa_1 > n_1$, but the critical thickness and the condition linking the refractive indices to one another are different than in the case of observation under unpolarized light.

Figures 4, 5, 6, 7:
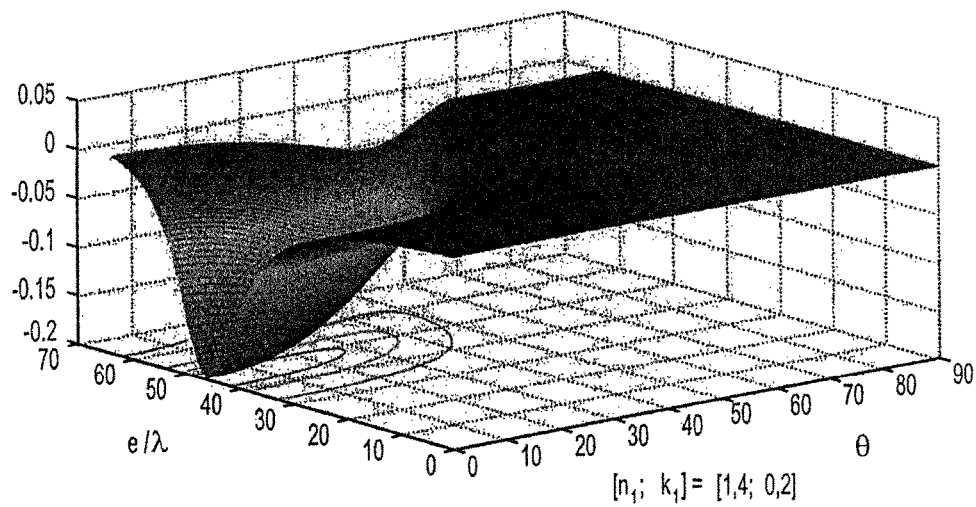

As shown in FIG. 7, it is possible to use a support having a contrast-amplifying layer which has a thickness gradient. The condition (3) will be satisfied, for at least one illumination wavelength, in a predetermined region of the support, which may be found by simple observation.

In order to move in the plane ($n_1$, $\kappa_1$), it is possible to adjust the composition of the contrast-amplifying layer—which may even in fact by a multilayer, thereby giving the designer great freedom—and/or the illumination wavelength throughout the range permitted by the optical elements of the system, generally from near UV ($\lambda=200$ nm) to near infrared ($\lambda=2$ µm). The UV and infrared wavelengths have the advantage of making it possible to exploit the natural absorption bands of the molecules visualized in order to obtain a better contrast and, where appropriate, a contrast specific for the species sought. By way of example, the Au curve in FIG. 6 shows the values of $n_1$ and $\kappa_1$ for a layer of gold as a function of the illumination wavelength which varies in the range 350-750 nm.

The case of gold is particularly interesting since it constitutes a norm for biological sensors. The case of a gold film consisting of nanoparticles is particularly advantageous since it is possible to adjust $n_1$ and $\kappa_1$ by adjusting the concentration and the density of the particles of which it is formed.

Figures 4, 5, 6, 7, 8:
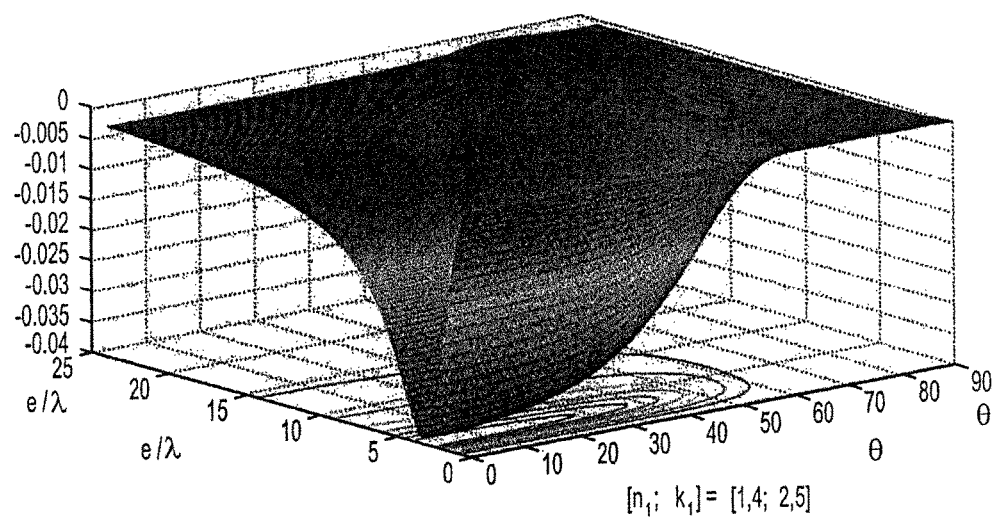

The principle that has just been described makes it possible to observe microscopic objects of low contrast. It also makes it possible to produce biochips for detecting and/or quantitatively determining chemical or biological species. For example, as illustrated in FIG. 8, it is possible to deposit a functionalization layer CF on the contrast-amplifying layer. The functionalization layer is brought into contact with a solution S, which is for example aqueous, containing the chemical or biological species to be detected ECD. The latter is bound by the functionalization layer and forms an additional thin layer CE, constituting the sample to be observed. In practice, in the case of a biochip, several different functionalization spots will be deposited, making it possible to selectively bind different chemical or biological species. By observing the biochip under a microscope, under the conditions described above, it is possible to easily identify the species actually present in the solution.

The sensitivity of the detection will be considerably improved if the species bound are themselves at least slightly optically absorbent for the useful wavelength of the illumination, for example if the imaginary part of their index is greater than 0.0001, and preferably greater than 0.001, and preferably greater than 0.01.

The contrast is also increased if the contrast-amplifying layer is deposited only in positions corresponding to said spots.

Preferably, outside the spots, a passivation layer which prevents the binding of any chemical or biological species contained in said solution can be envisioned. A polyethylene glycol, a fluorinated polymer or a fluorinated alkyl, for example functionalized with thiols in the case of gold, can, for example, be used. This passivation layer may be deposited by vapor deposition after the production of the spots.

When it is desired to detect or deposit chemical or biological species, it is also possible to use a substrate only provided with a functionalization layer.

Figures 4, 5, 6, 7, 8, 9:
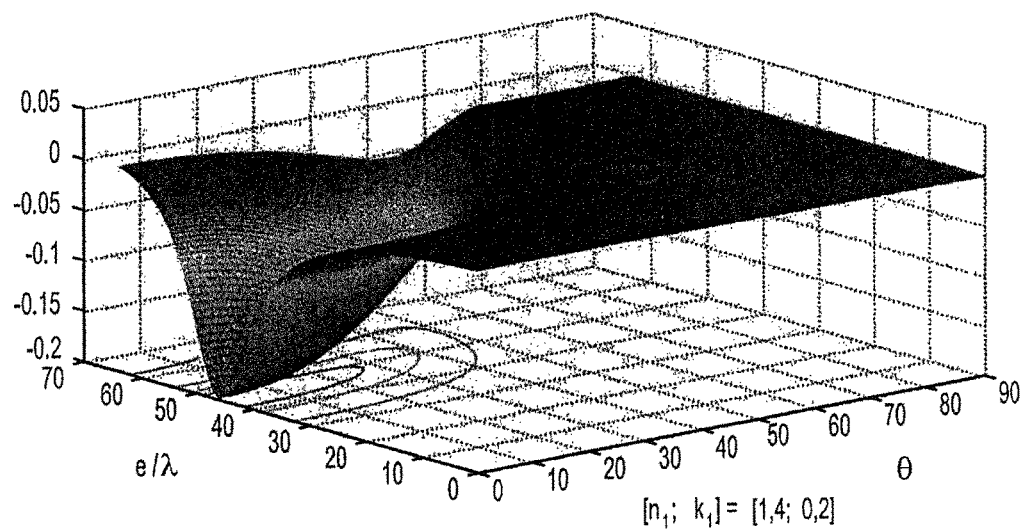

According to a first embodiment, illustrated in FIG. 9, the functionalization layer is brought into contact with a solution containing a chemical or biological species ECD to be detected or quantitatively determined, labeled with metal nanoparticles NPM and capable of binding to said functionalization layer so as to form a metallic layer CM. This layer may in reality be discontinuous, but it appears continuous on the scale of the wavelength of visible light (several hundred nanometers), with an effective thickness which may be a fraction of the diameter of the nanoparticle, and with an effective refractive index. The observation is carried out in the manner described above, the metallic layer thus formed serving as both contrast-amplifying layer and sample. For a predetermined contact time between the solution and the functionalized layer, the thickness of the metallic layer depends on the content of chemical or biological species, which makes it possible to carry out a quantitative determination.

As a variant, the metal nanoparticles can be replaced with an absorbent label, for example a fluorescent molecule (it should be noted that the fluorescence, per se, is not exploited, but a fluorescent molecule is strongly absorbent).

The drawback of the first embodiment is that it allows only the detection of a labeled chemical or biological species. The following embodiments do not have this drawback.

Figures 4, 5, 6, 7, 8, 9, 10:
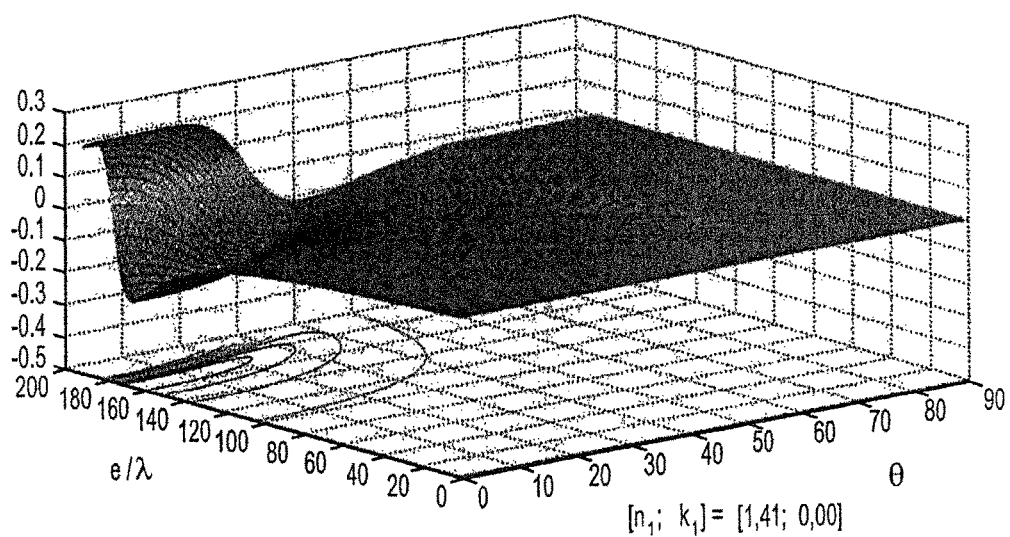

According to the second embodiment (FIG. 10), the functionalized layer is placed in contact with a first solution S1 containing the chemical or biological species to be detected or quantitatively determined, so as to form an "intermediate" layer CI. This intermediate layer is not observable. In order to reveal it, it is brought into contact with a second solution S2, containing an "auxiliary" chemical or biological species ECA, labeled with metal nanoparticles (or an absorbent label) and capable of binding to said intermediate layer so as to form the metallic (or absorbent) layer CM.

The technique can be quantitative if the species to be detected is present in sufficient amount to saturate the functionalization layer and, on the other hand, the auxiliary species is present in excess. In this case, in fact, the effective thickness and the effective index of the layer CM—and therefore the intensity of the light signal observed—will depend on the concentration of the species to be detected.

This second embodiment can be used only if the chemical or biological species to be detected has at least two active sites; it does not therefore apply, for example, to haptens. In addition, it is quite complex to implement.

The following embodiments do not have this drawback.

Figures 4, 5, 6, 7, 8, 9, 10, 11:
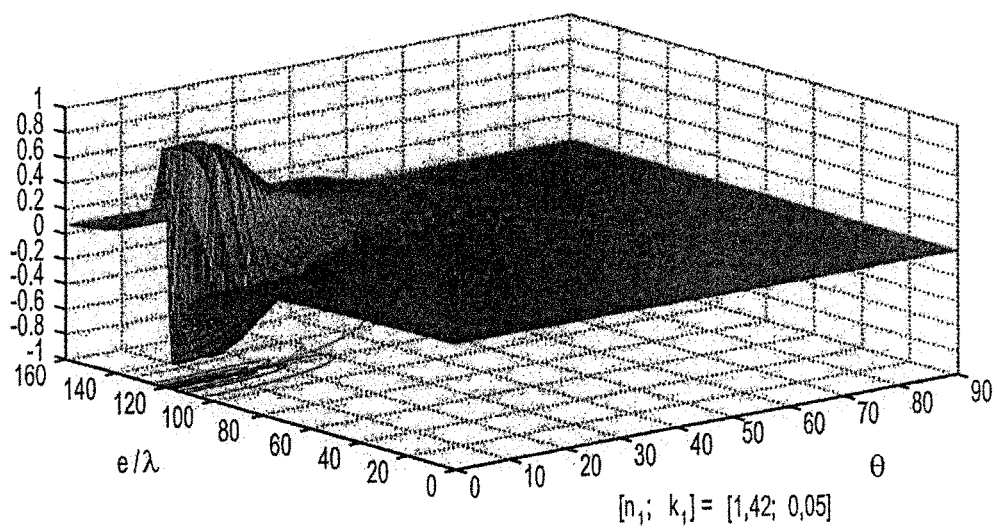

According to the third embodiment (FIG. 11), the functionalized layer is placed in contact with a first solution (S1) containing a chemical or biological species, termed intermediate species ECI, labeled with metal nanoparticles or an absorbent label and capable of binding to said functionalization layer so as to form said continuous or discontinuous, metallic or absorbent layer (CM). Next, the resulting assembly is brought into contact with a second solution (S2) containing the chemical or biological species to be detected or quantitatively determined, which has an affinity with said functionalization layer that is greater than that of said intermediate species. Thus, the intermediate species is displaced and said metallic or absorbent layer is at least partially eliminated, which is reflected by a decrease in the light signal. The technique is qualitative rather than quantitative; it is therefore more suitable for detection than for quantitative determination. An advantage of this approach is that its two steps can be dissociated: the supports can be provided with the layer CM already formed, ready to be used as chemical or biological sensors.

Figures 4, 5, 6, 7, 8, 9, 10, 11, 12:
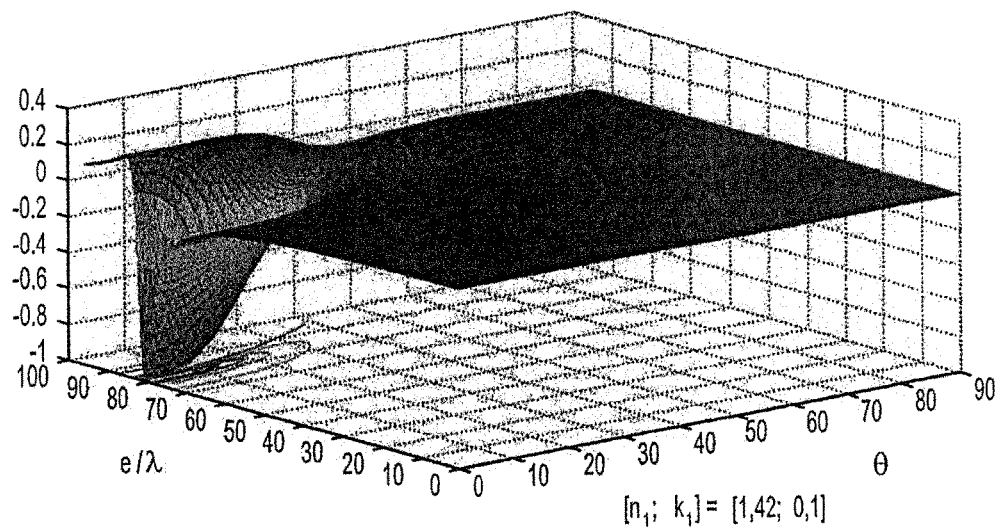
Figures 4, 5, 6, 7, 8, 9, 10, 11, 12, 13:
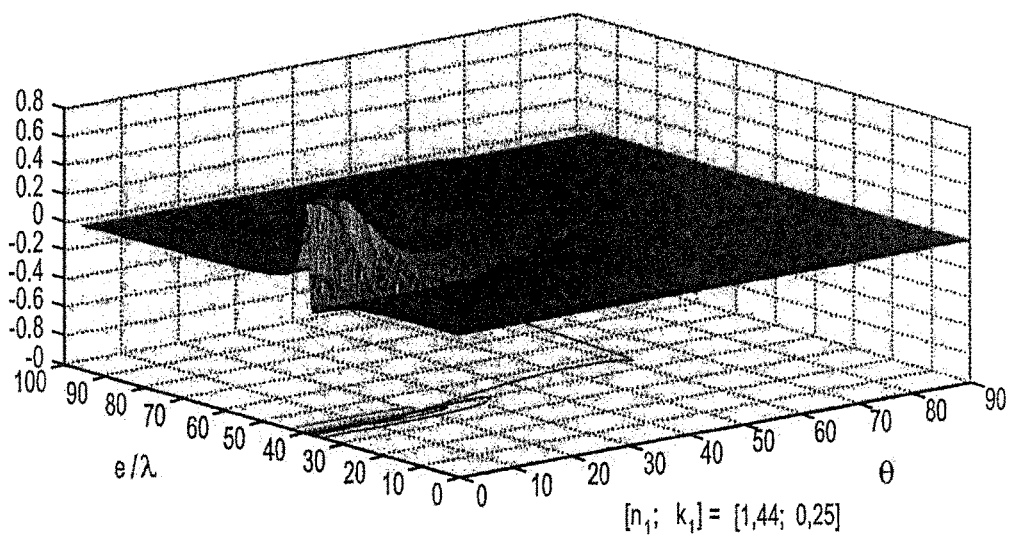
Figures 4, 5, 6, 7, 8, 9, 10, 11, 12, 13, 14:
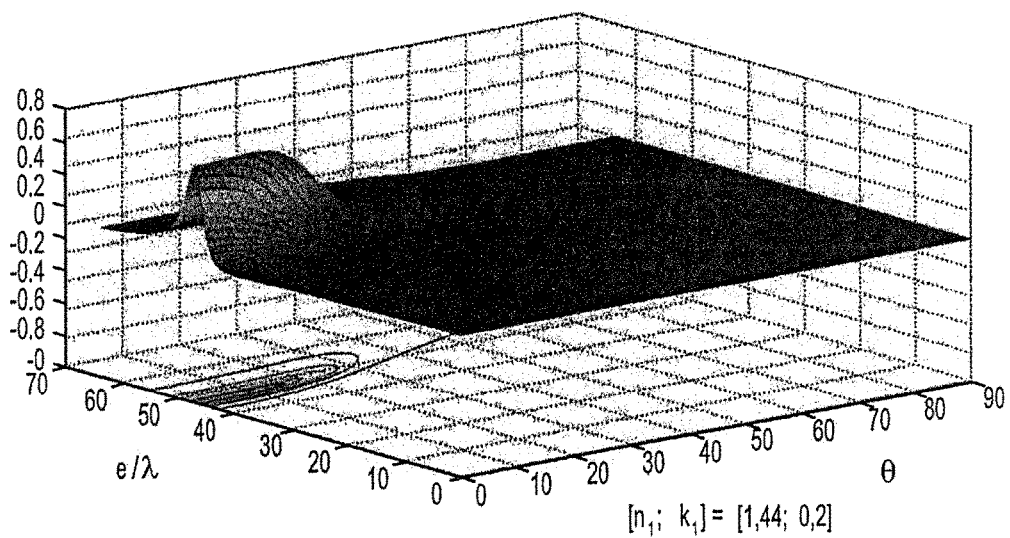
Figures 4, 5, 6, 7, 8, 9, 10, 11, 12, 13, 14, 15:
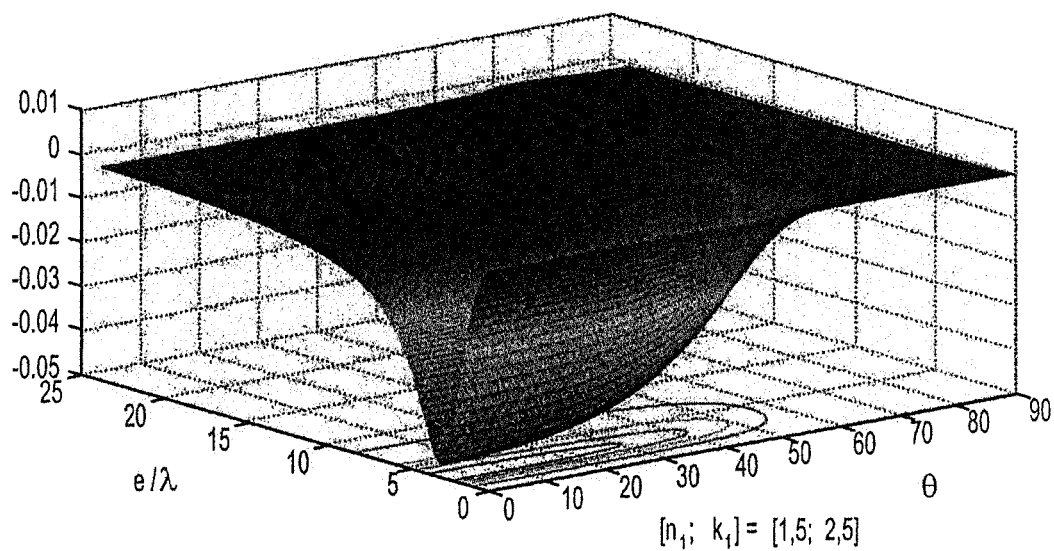
Figures 4, 5, 6, 7, 8, 9, 10, 11, 12, 13, 14, 15, 16:
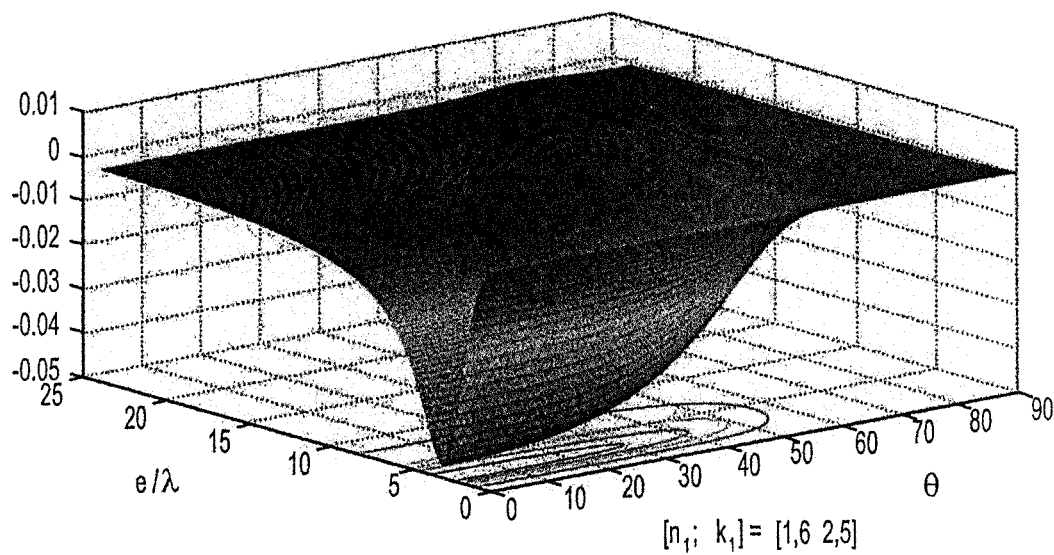
Figures 4, 5, 6, 7, 8, 9, 10, 11, 12, 13, 14, 15, 16, 17:
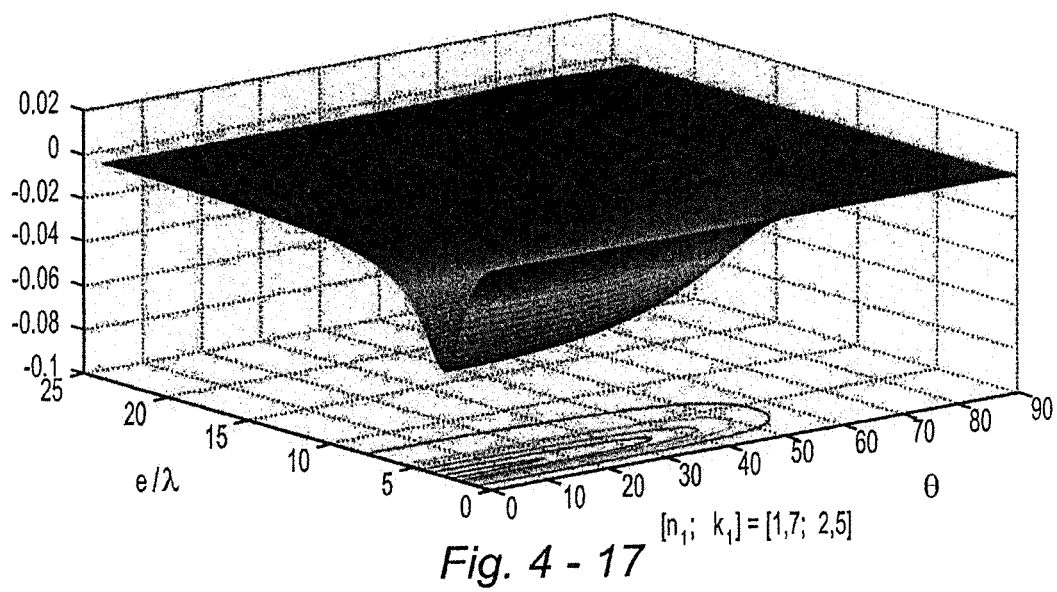
Figures 4, 5, 6, 7, 8, 9, 10, 11, 12, 13, 14, 15, 16, 17, 18:
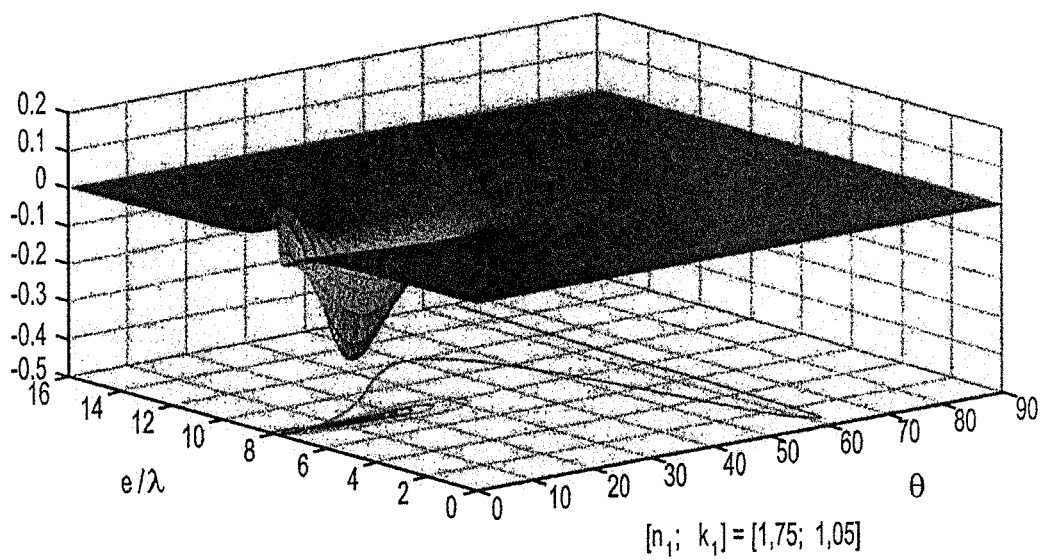
Figures 4, 5, 6, 7, 8, 9, 10, 11, 12, 13, 14, 15, 16, 17, 18, 19:
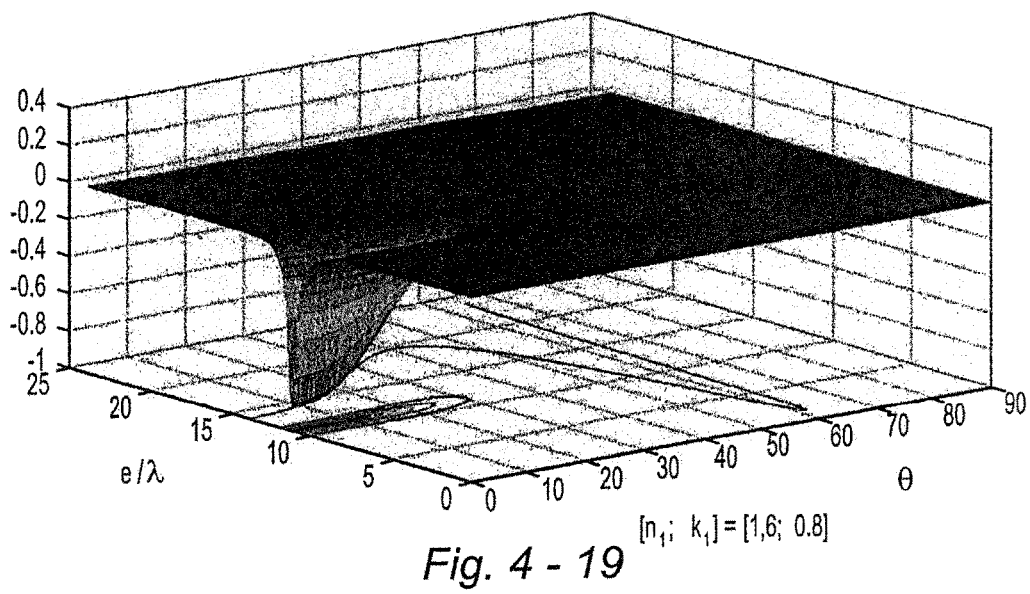
Figures 4, 5, 6, 7, 8, 9, 10, 11, 12, 13, 14, 15, 16, 17, 18, 19, 20:
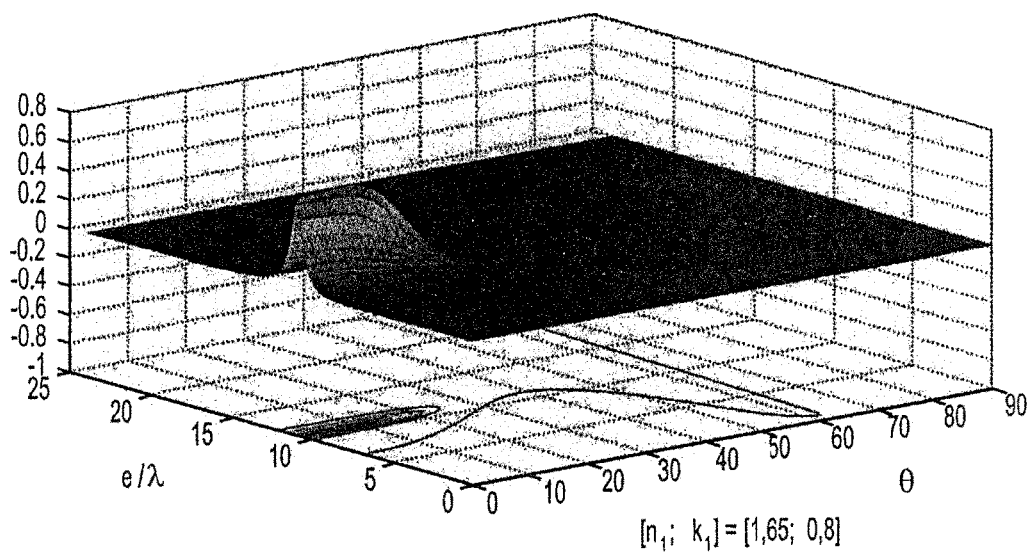
Figures 4, 5, 6, 7, 8, 9, 10, 11, 12, 13, 14, 15, 16, 17, 18, 19, 20, 21:
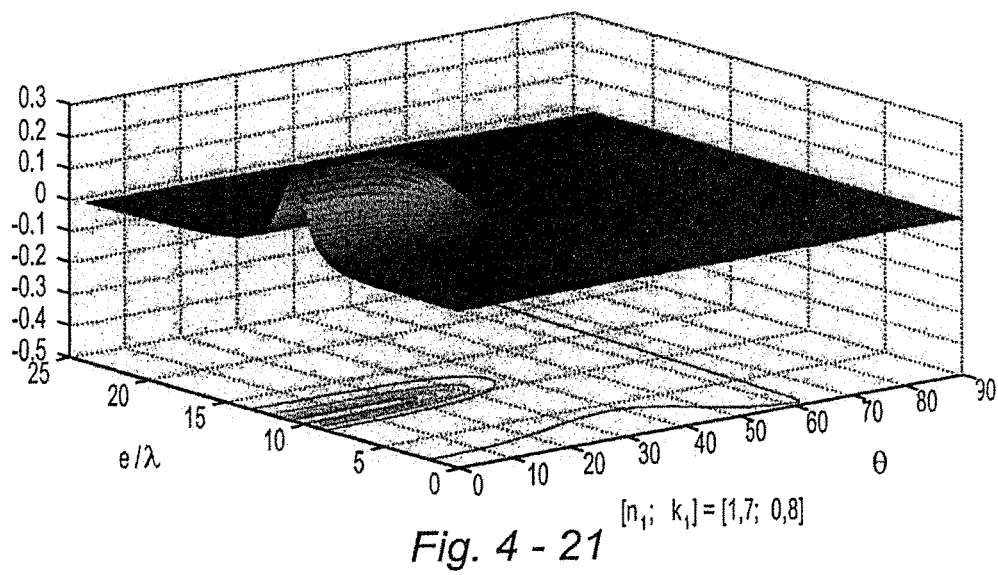
Figures 4, 5, 6, 7, 8, 9, 10, 11, 12, 13, 14, 15, 16, 17, 18, 19, 20, 21, 22:
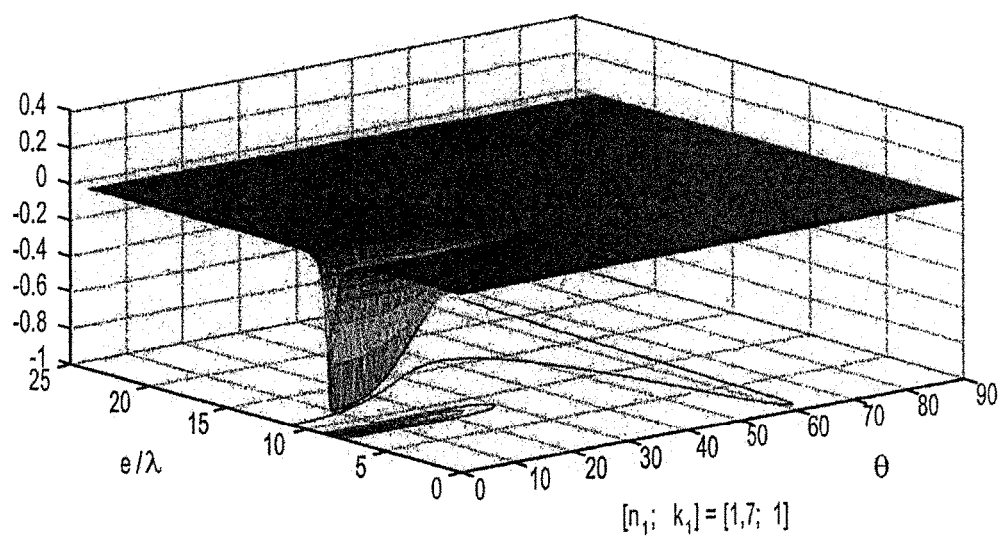
Figures 4, 5, 6, 7, 8, 9, 10, 11, 12, 13, 14, 15, 16, 17, 18, 19, 20, 21, 22, 23:
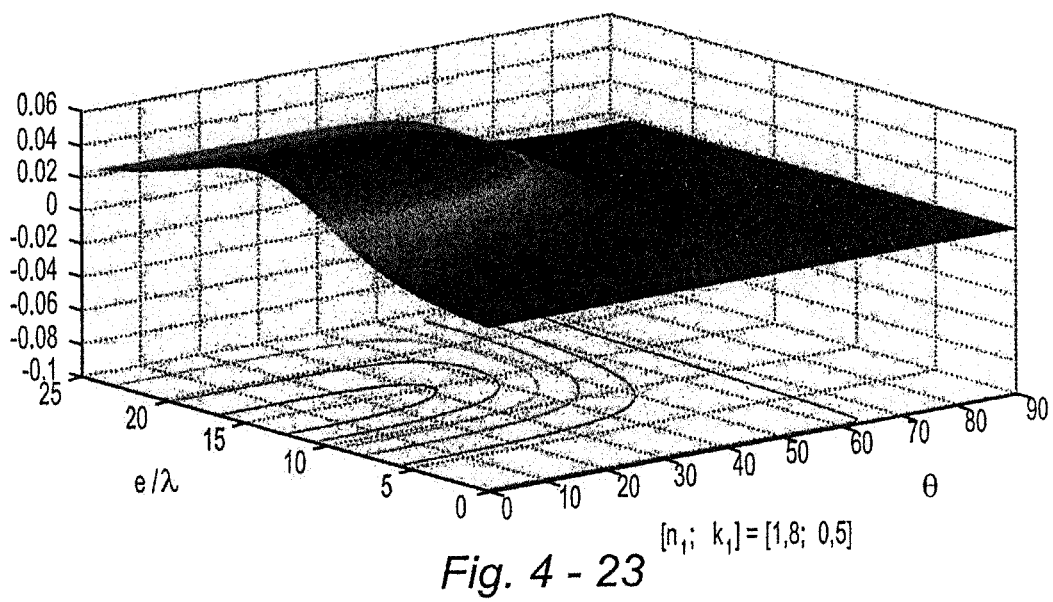
Figures 4, 5, 6, 7, 8, 9, 10, 11, 12, 13, 14, 15, 16, 17, 18, 19, 20, 21, 22, 23, 24:
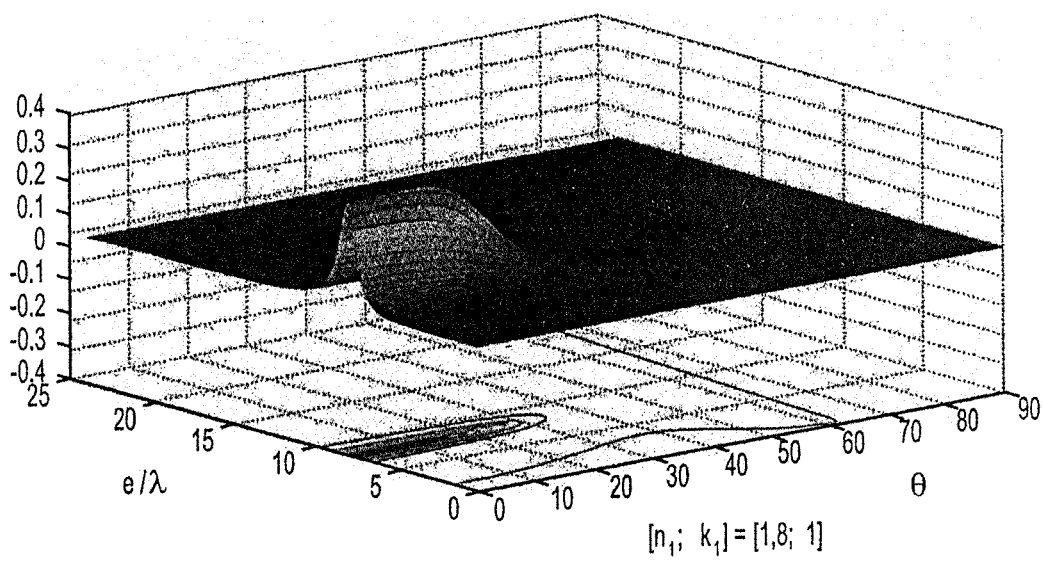
Figures 4, 5, 6, 7, 8, 9, 10, 11, 12, 13, 14, 15, 16, 17, 18, 19, 20, 21, 22, 23, 24, 25:
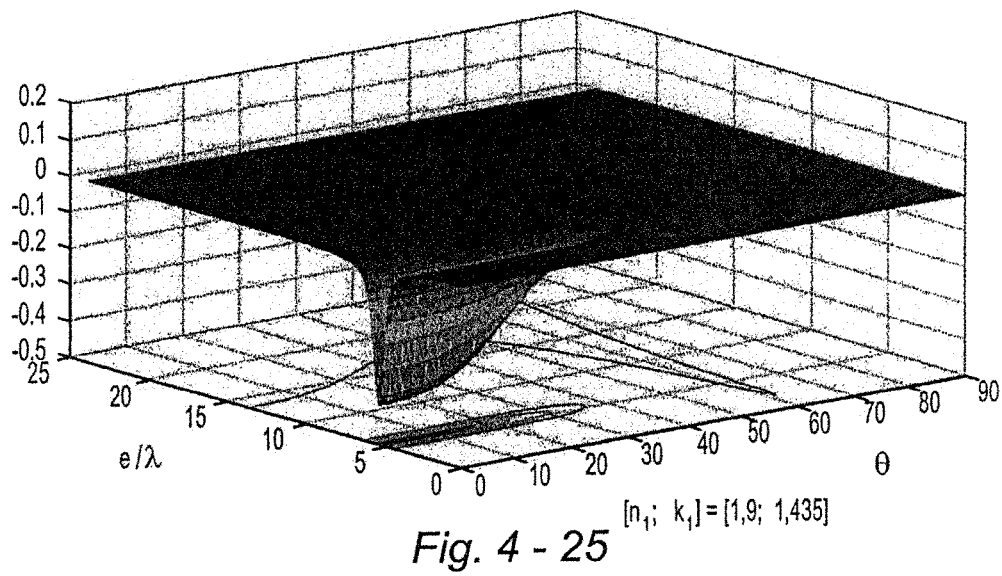
Figures 4, 5, 6, 7, 8, 9, 10, 11, 12, 13, 14, 15, 16, 17, 18, 19, 20, 21, 22, 23, 24, 25, 26:
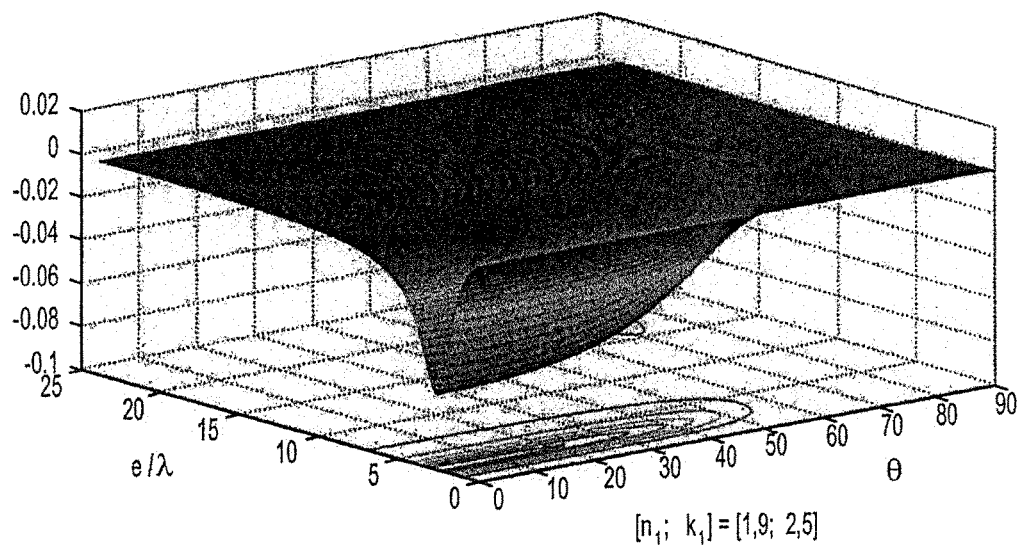
Figures 4, 5, 6, 7, 8, 9, 10, 11, 12, 13, 14, 15, 16, 17, 18, 19, 20, 21, 22, 23, 24, 25, 26, 27:
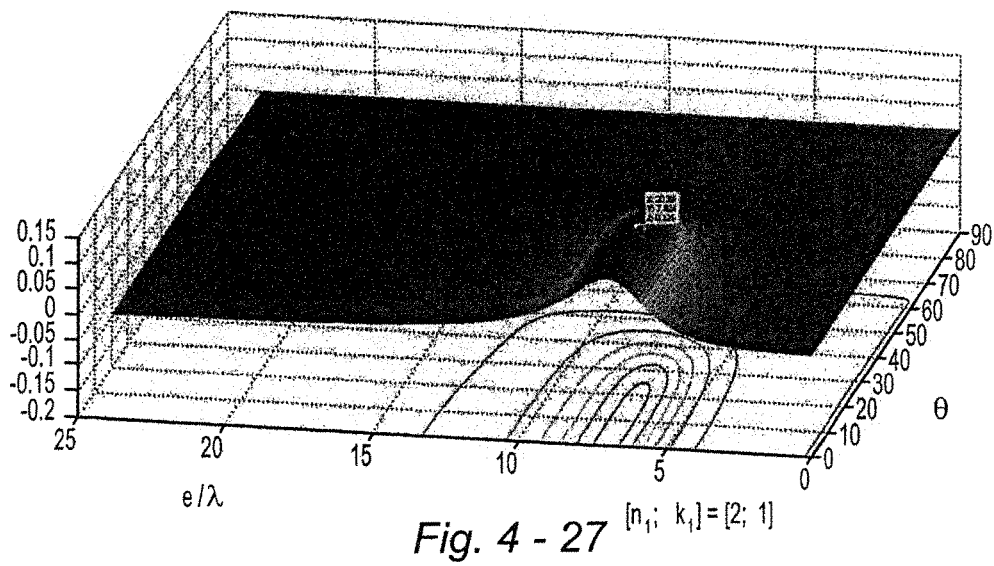
Figures 4, 5, 6, 7, 8, 9, 10, 11, 12, 13, 14, 15, 16, 17, 18, 19, 20, 21, 22, 23, 24, 25, 26, 27, 28:
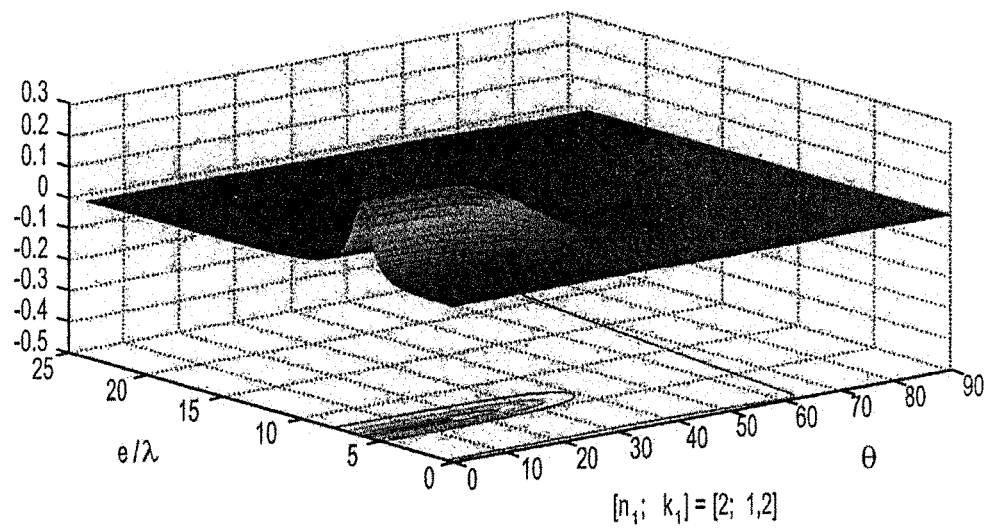
Figures 4, 5, 6, 7, 8, 9, 10, 11, 12, 13, 14, 15, 16, 17, 18, 19, 20, 21, 22, 23, 24, 25, 26, 27, 28, 29:
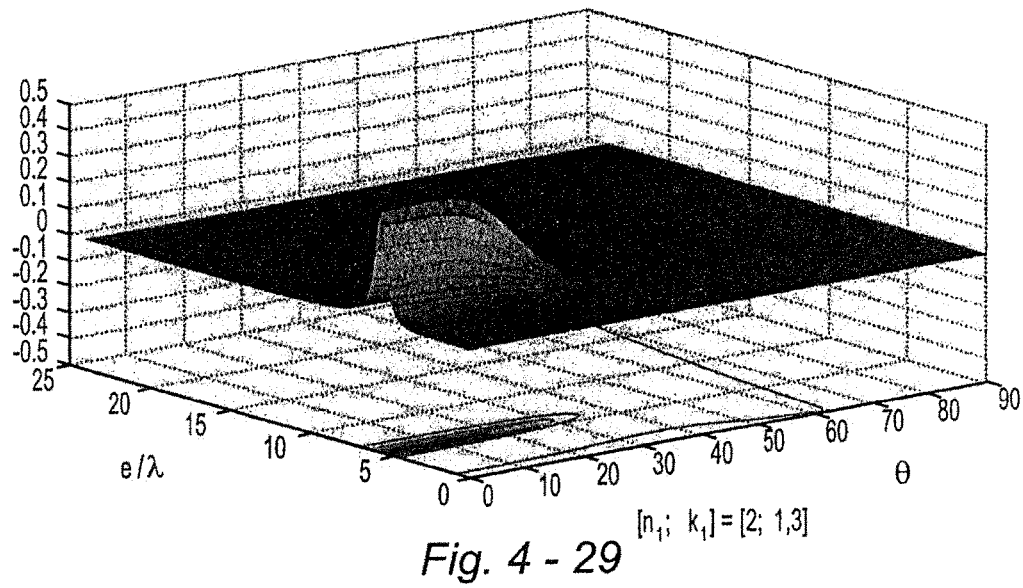
Figures 4, 5, 6, 7, 8, 9, 10, 11, 12, 13, 14, 15, 16, 17, 18, 19, 20, 21, 22, 23, 24, 25, 26, 27, 28, 29, 30:
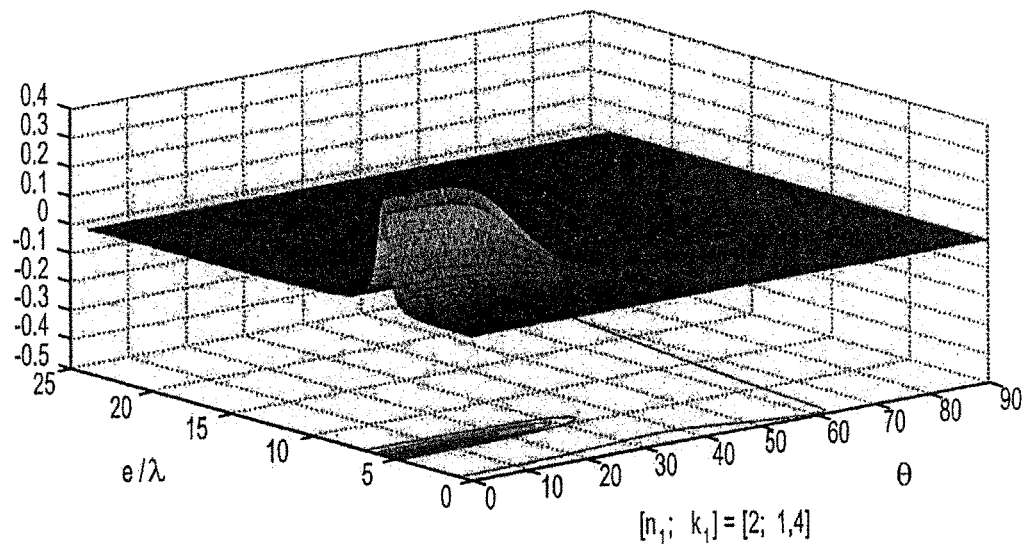
Figures 4, 5, 6, 7, 8, 9, 10, 11, 12, 13, 14, 15, 16, 17, 18, 19, 20, 21, 22, 23, 24, 25, 26, 27, 28, 29, 30, 31:
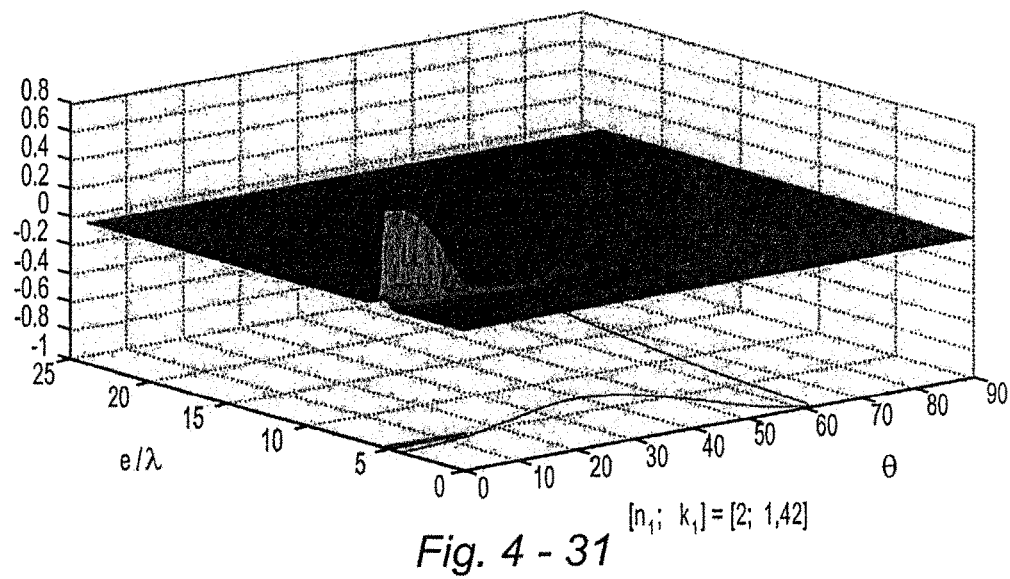
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32:
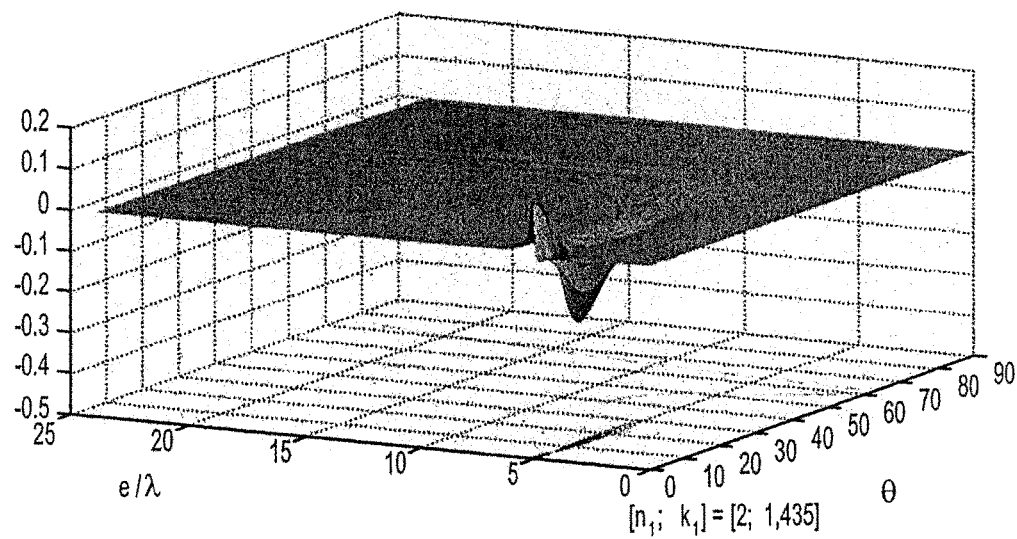
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33:
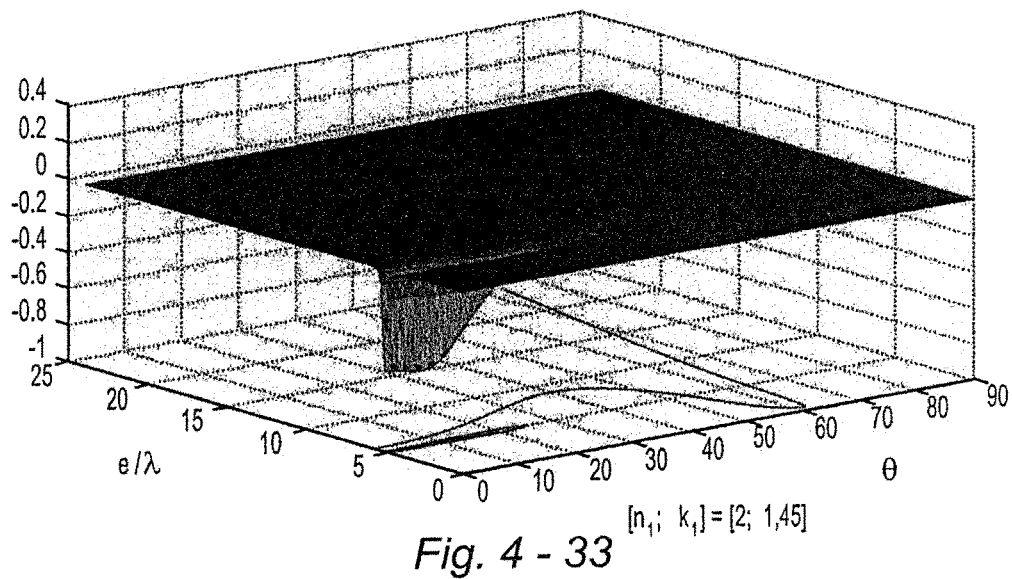
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34:
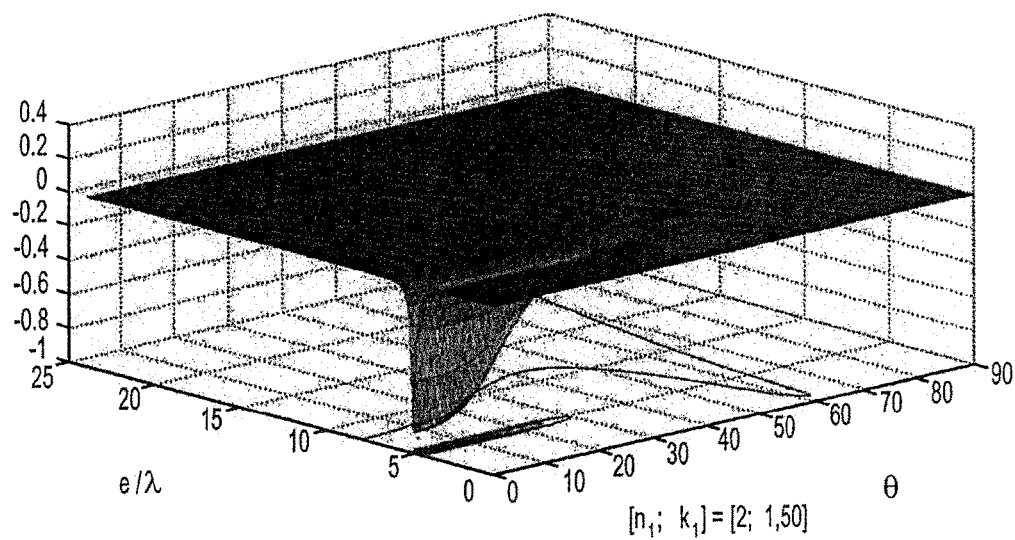
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
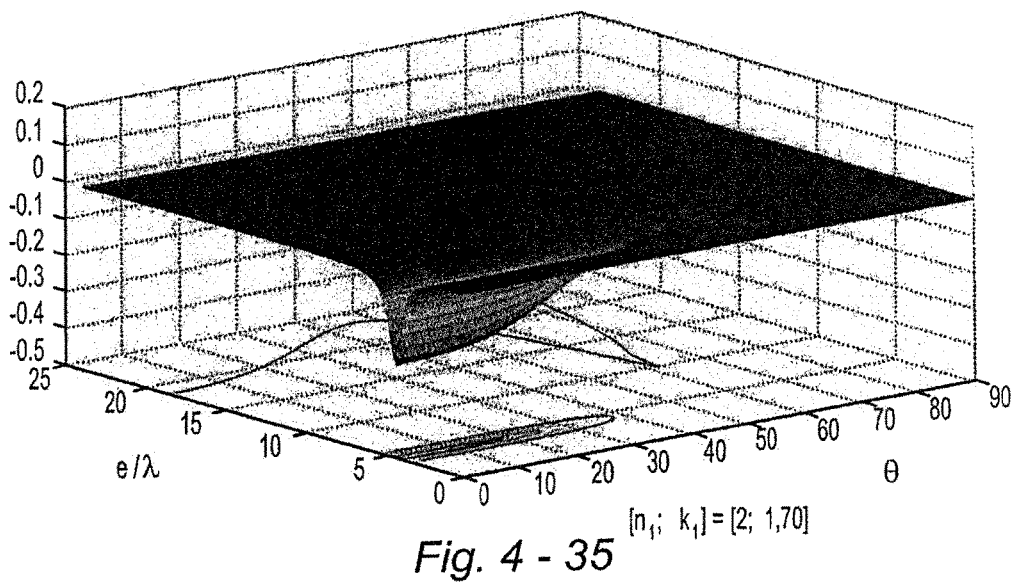
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
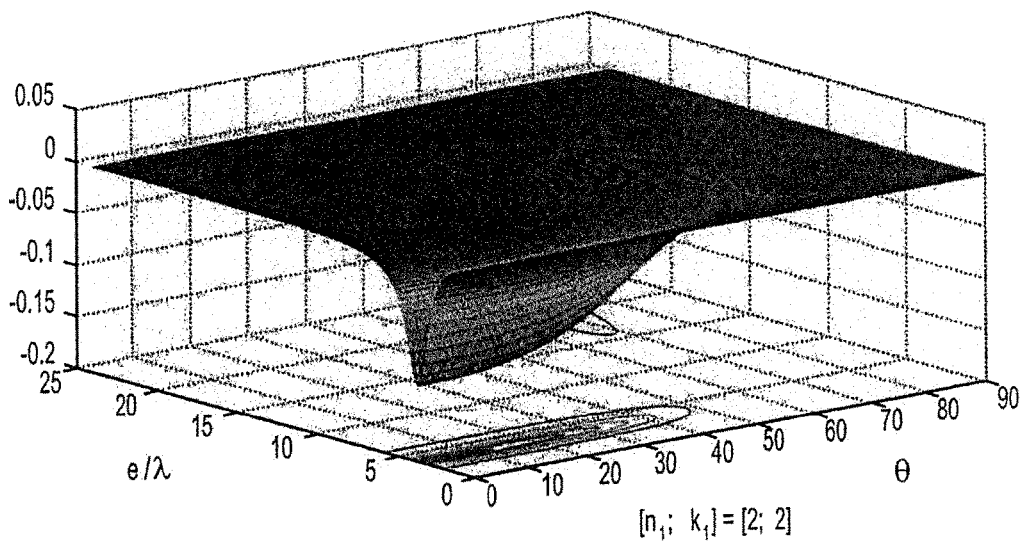
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37:
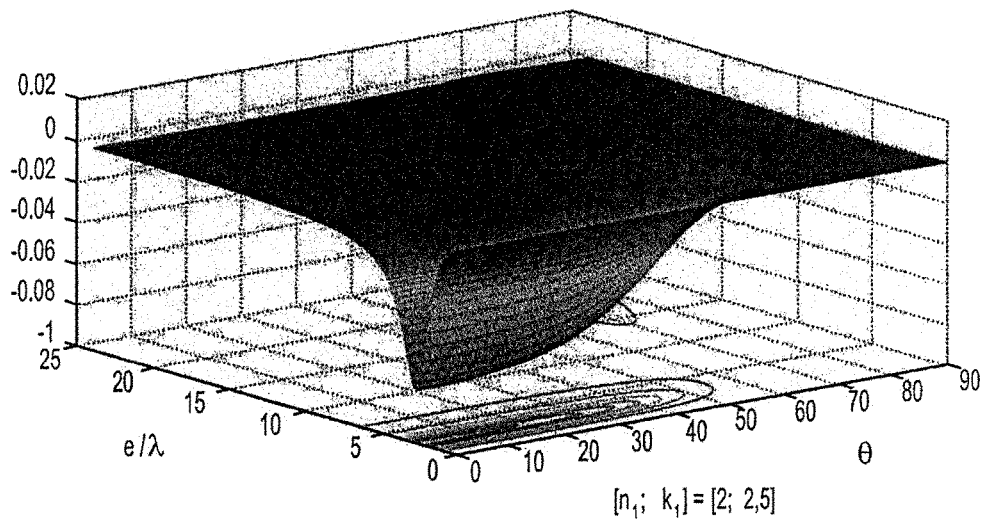
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
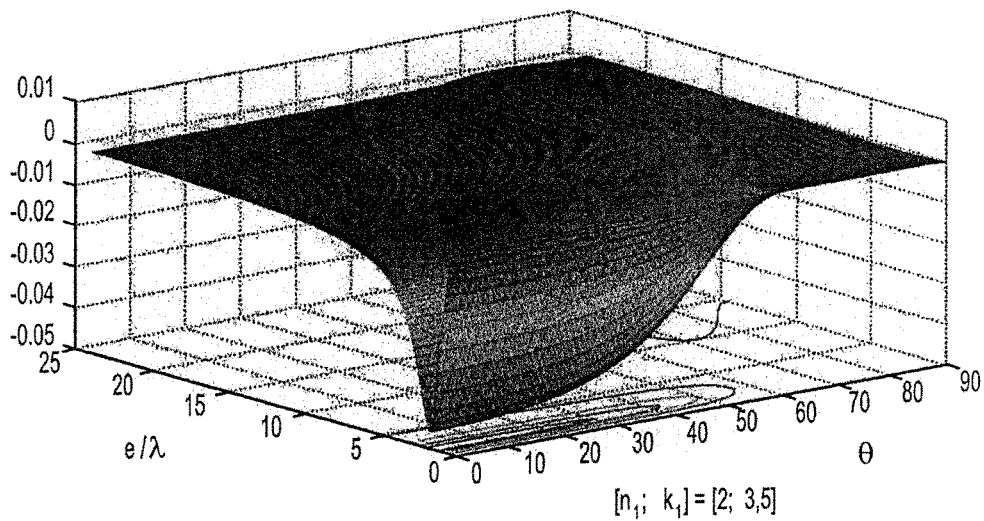
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
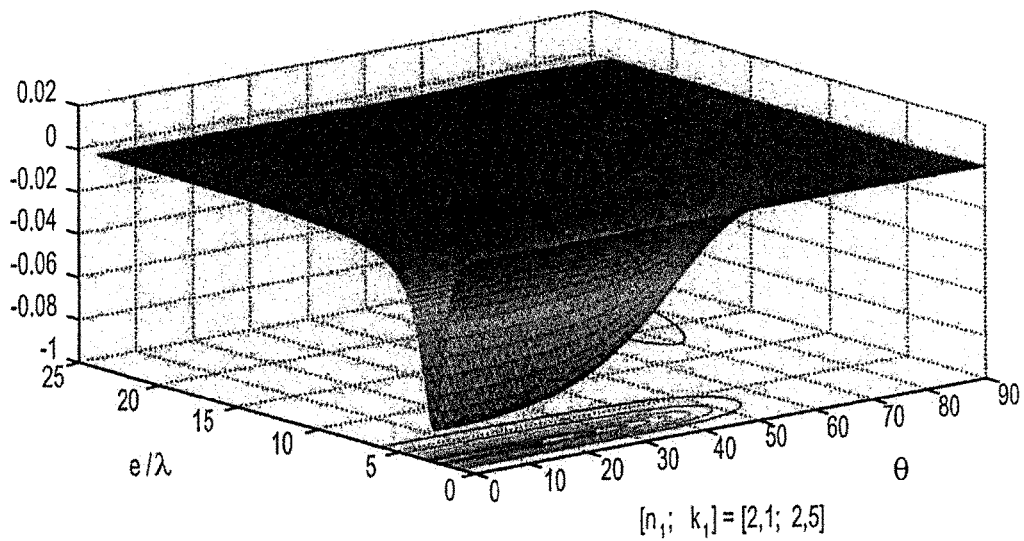
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
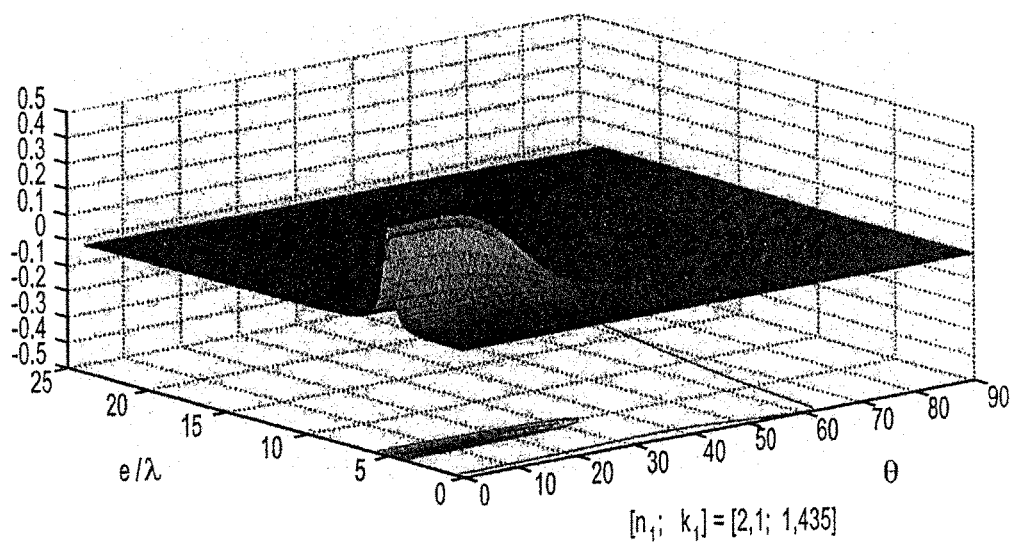
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
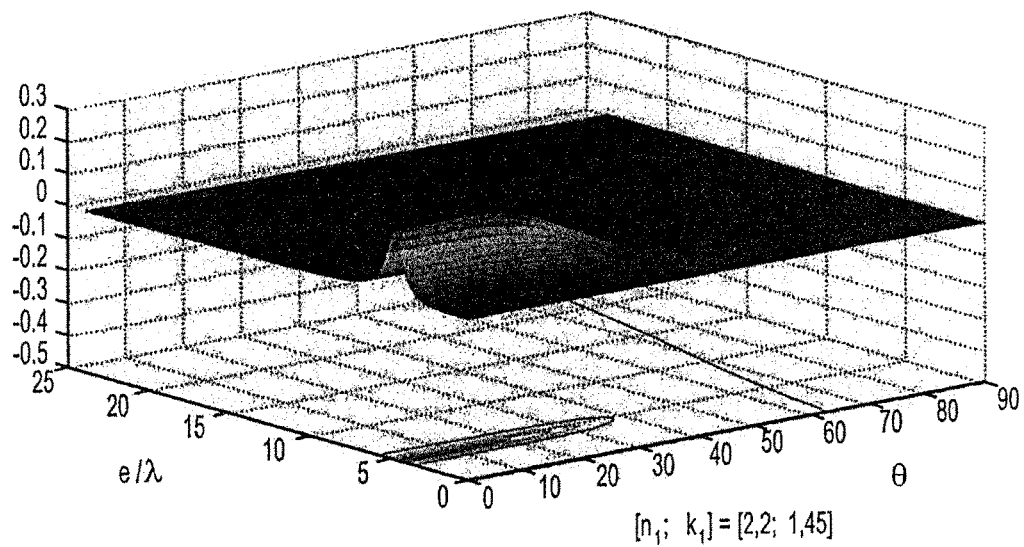
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
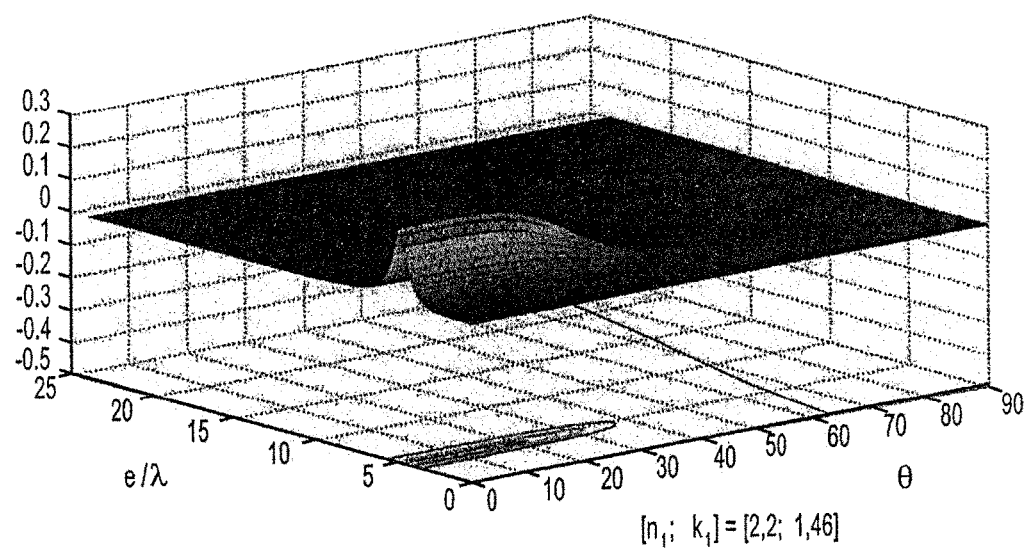
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43:
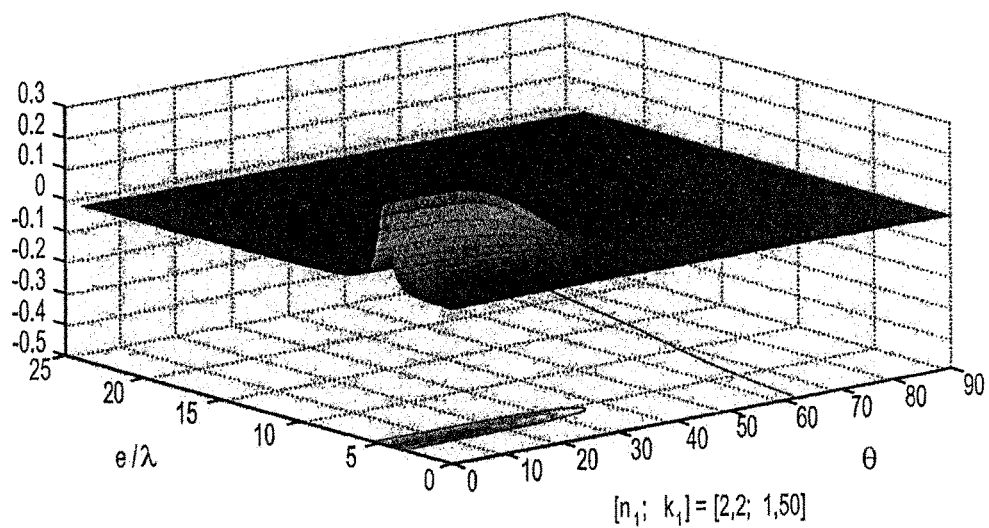
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
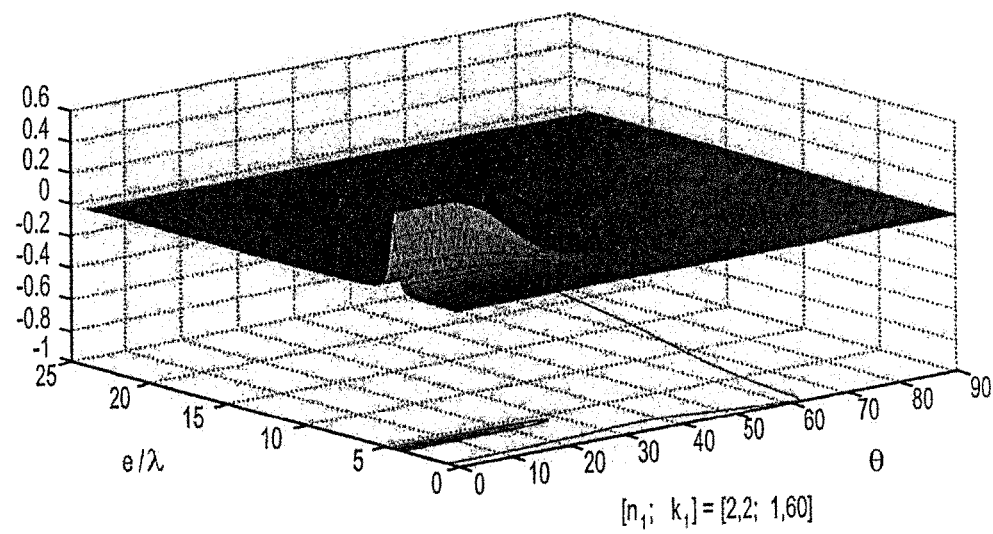
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45:
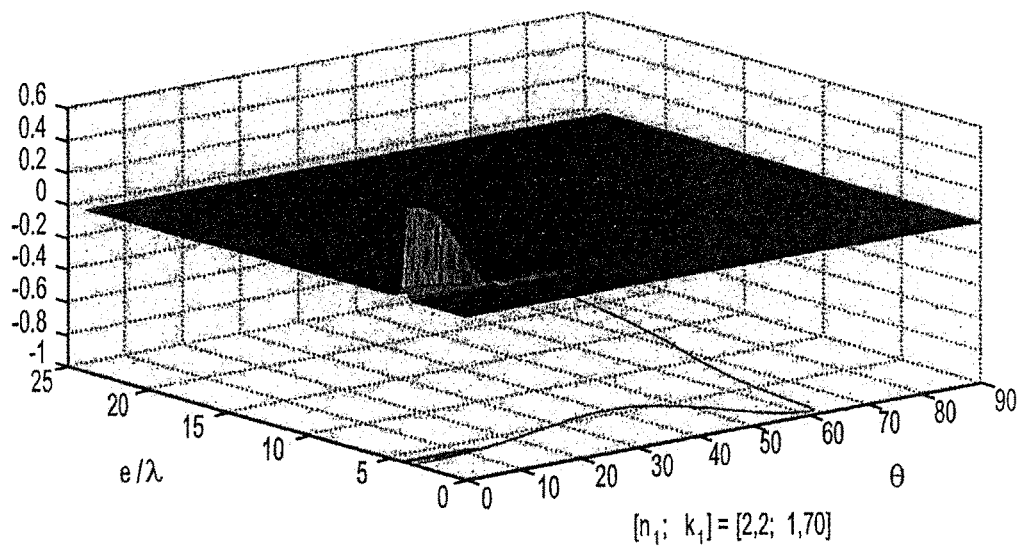
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46:
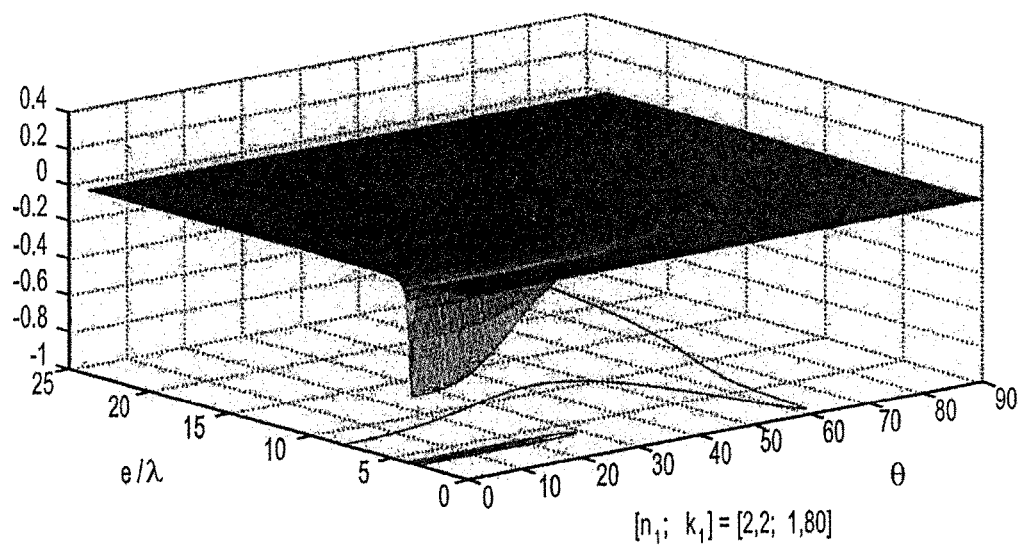
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47:
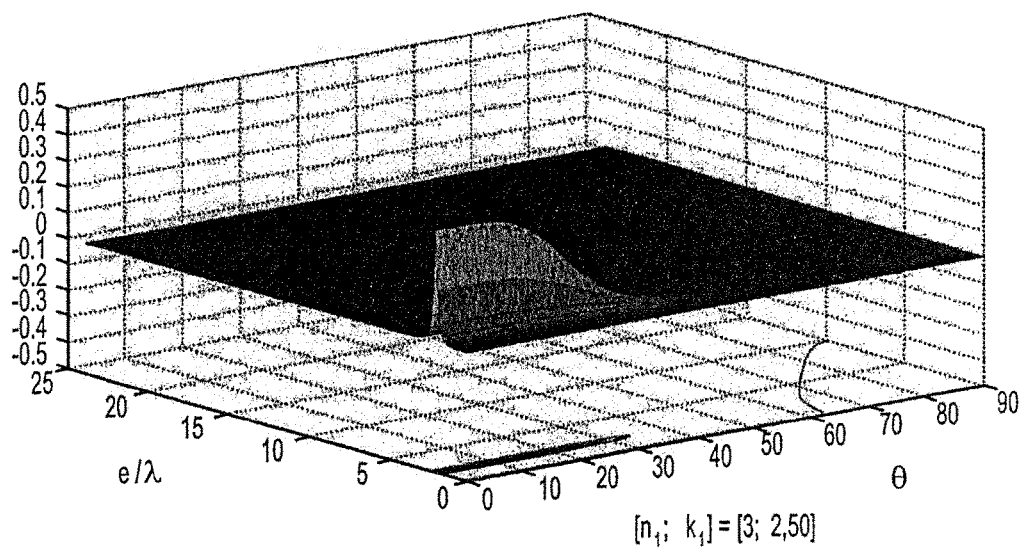
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48:
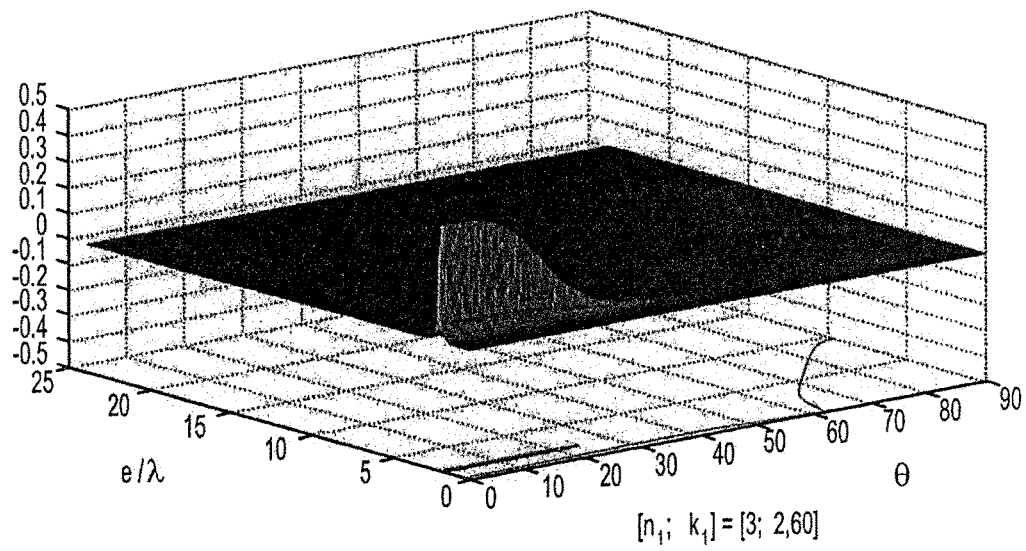
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49:
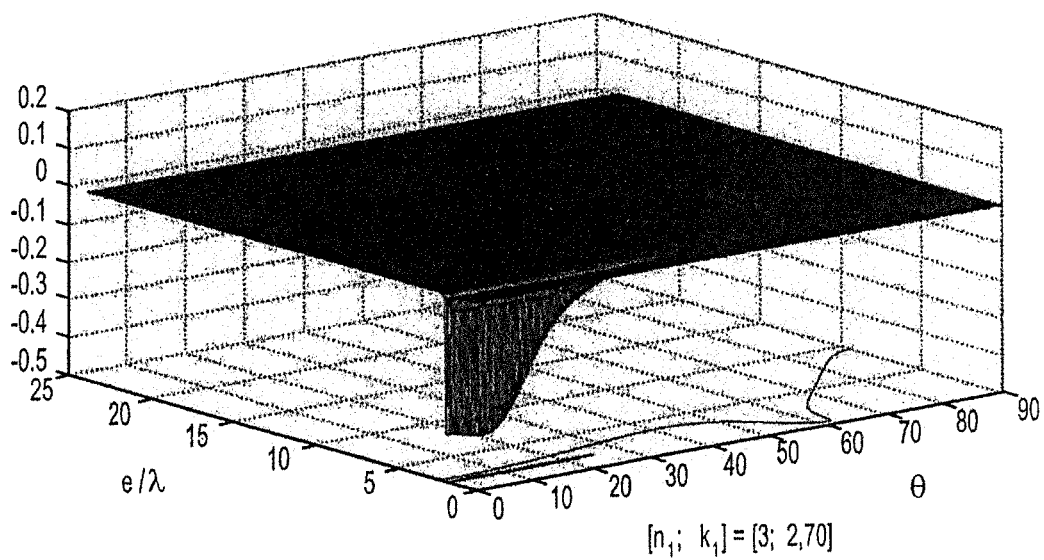
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50:
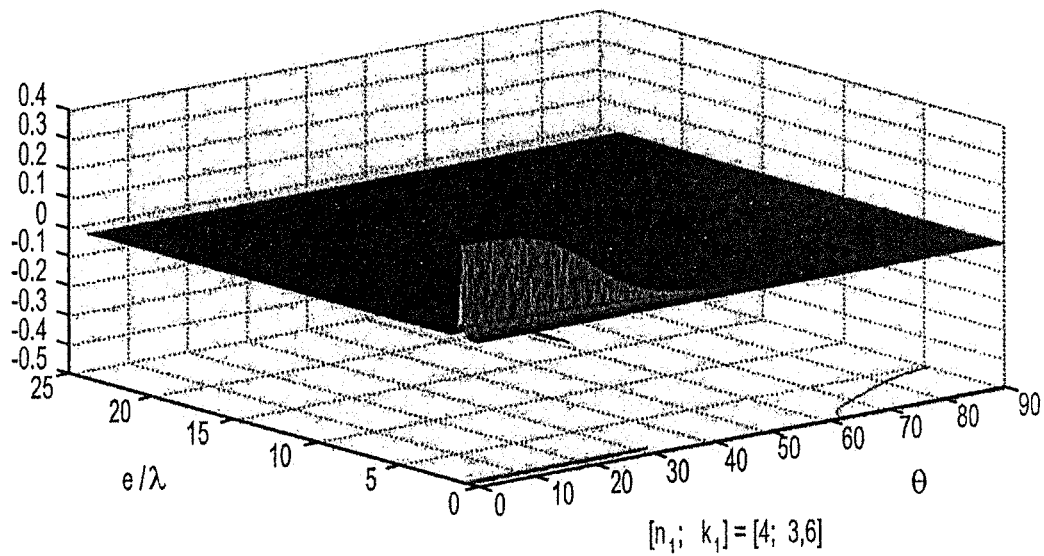
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51:
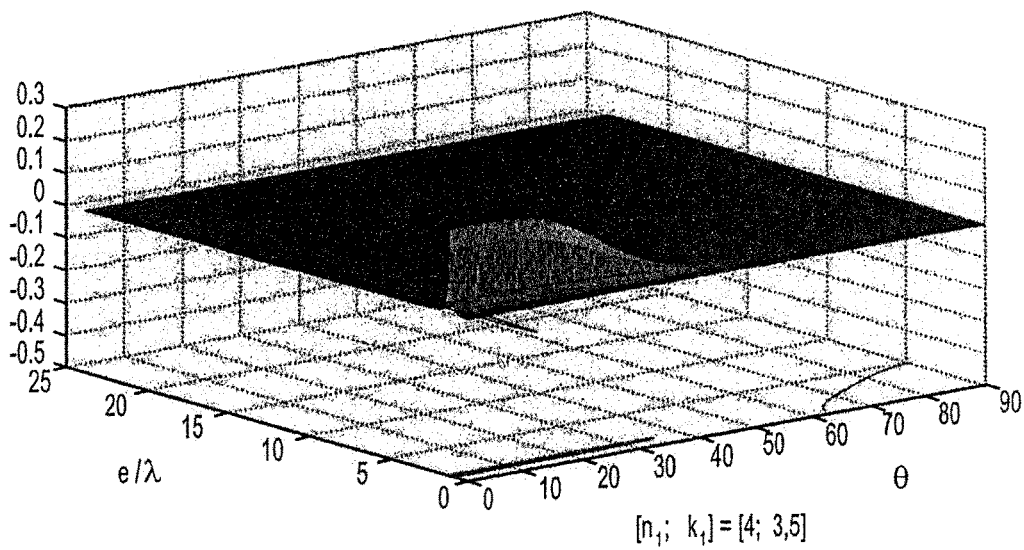
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52:
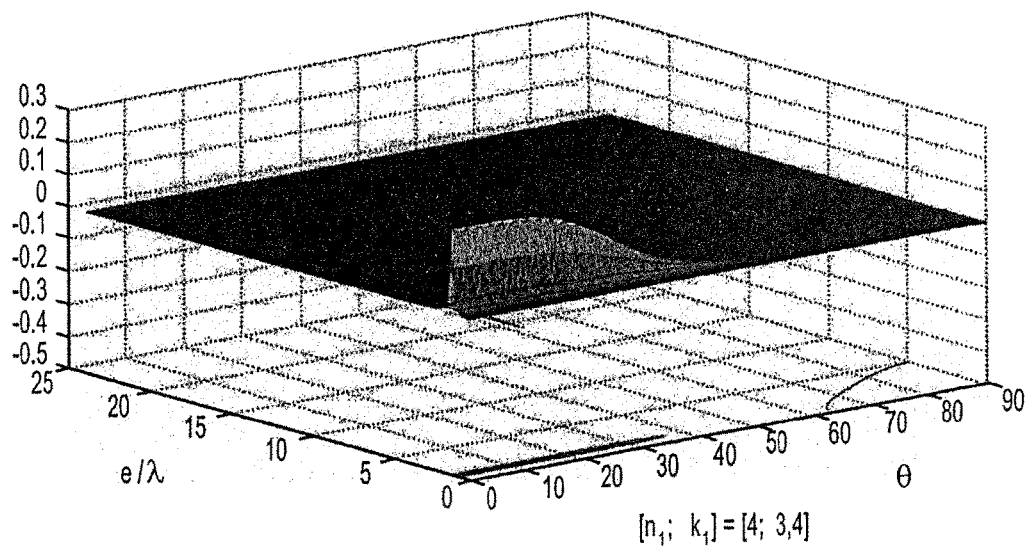
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53:
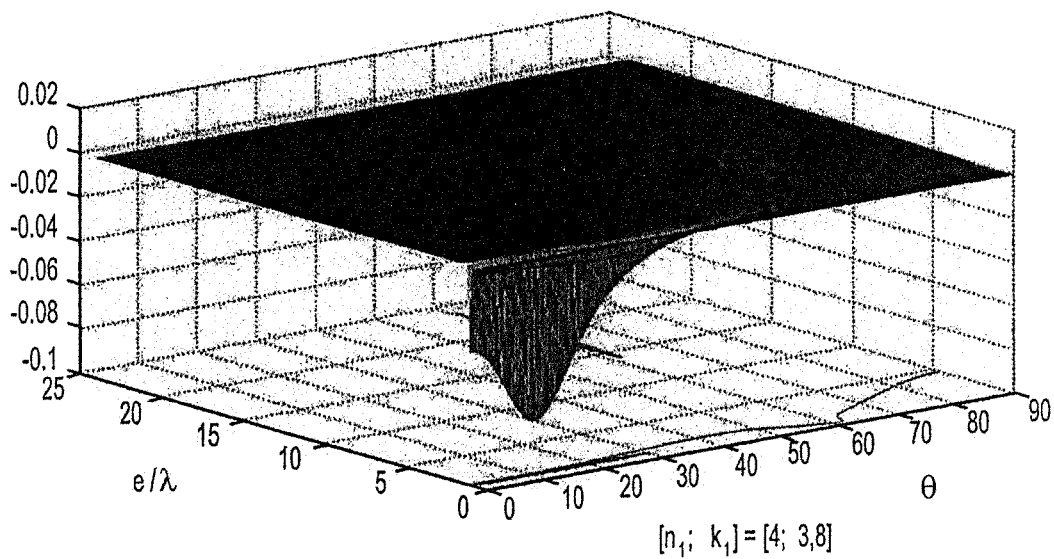
Figures 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54:
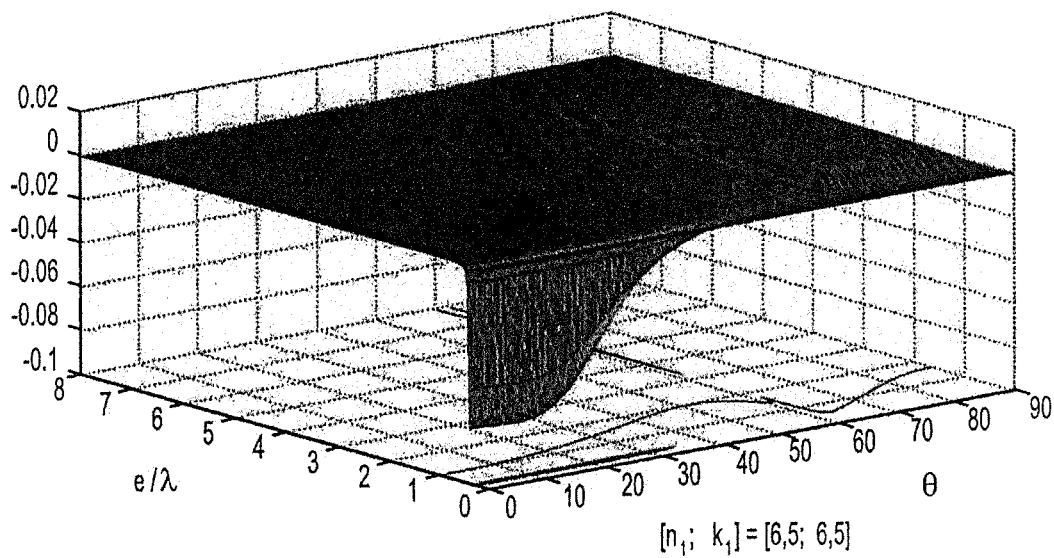
Figures 4, 55:
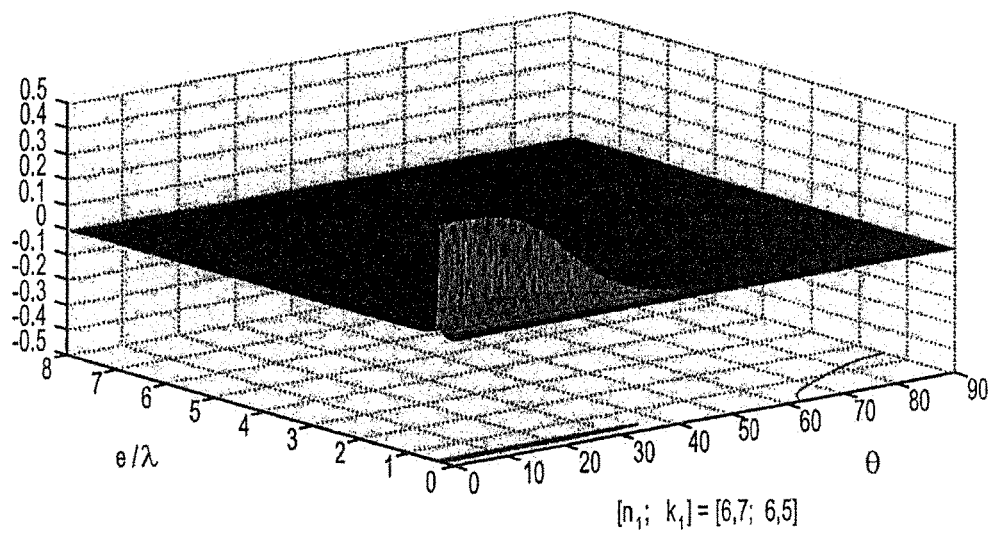
Figures 4, 56:
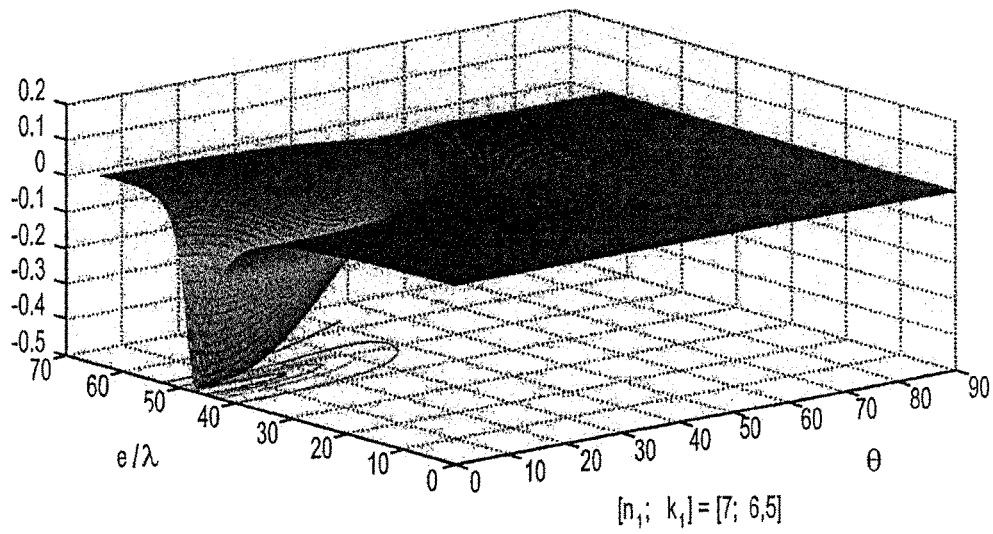
Figure 6:
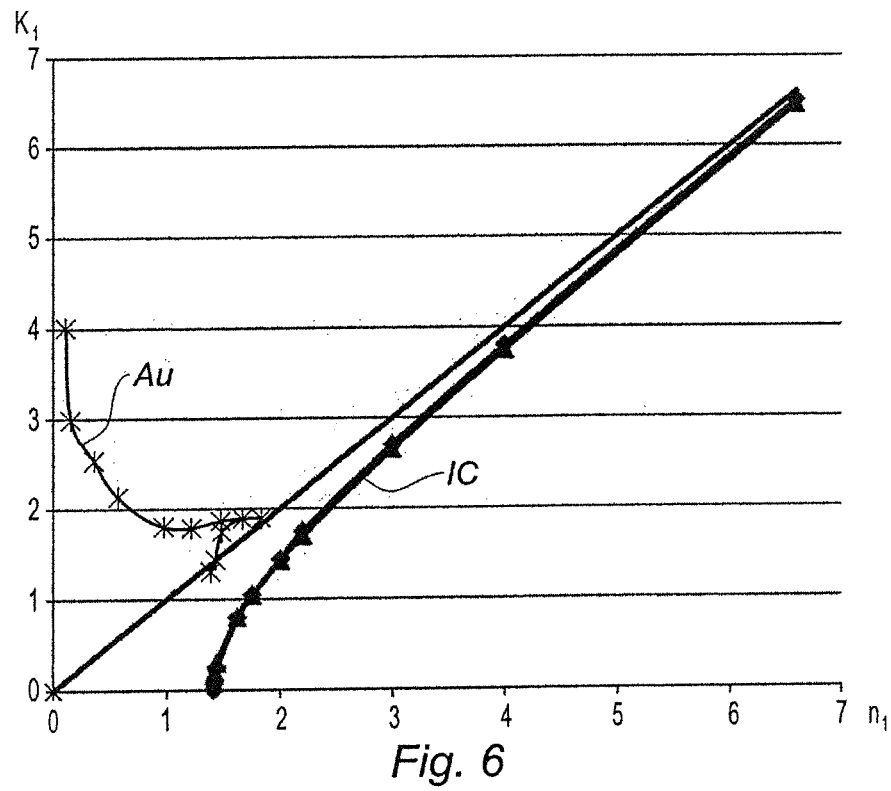
FIG. 6 locates a layer of gold in the plane n-κ, at various illumination wavelengths.
Figure 7:
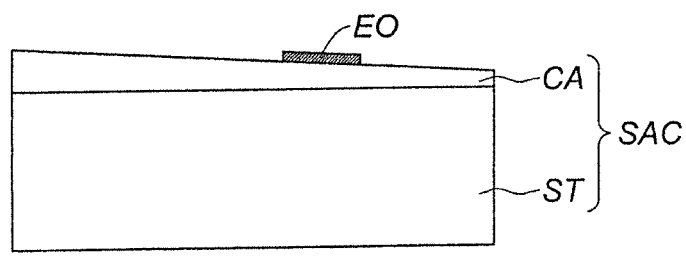
FIG. 7 represents a contrast-amplifying layer having a thickness gradient.
Figure 8:
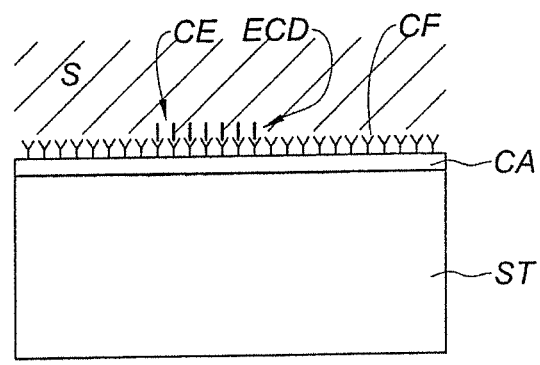
FIG. 8 represents a functionalized contrast-amplifying layer.
Figure 9:
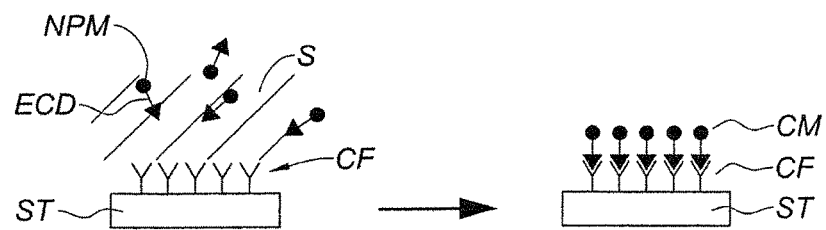
FIGS. 9-12 illustrate respectively the first, second, third and fourth embodiment of a process for detecting or quantitatively determining at least one chemical or biological species according to the invention.
Figure 10:
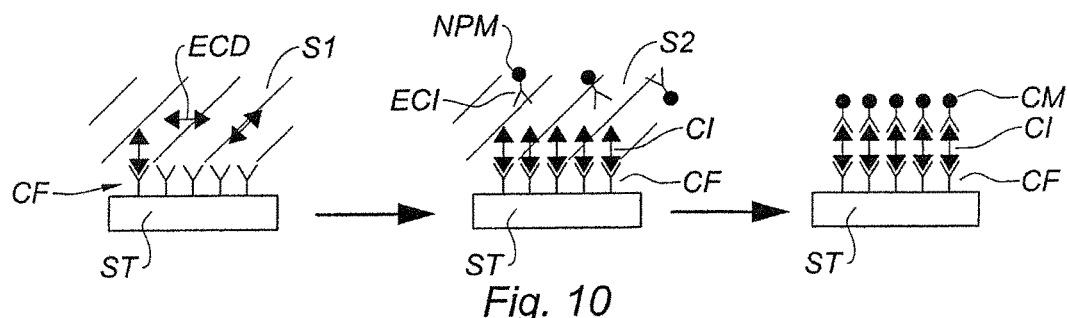
Figure 11:
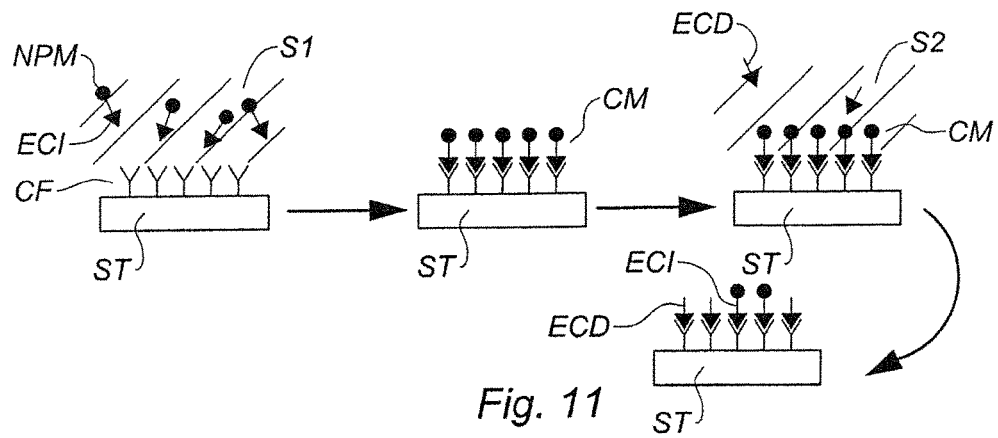
Figure 12:
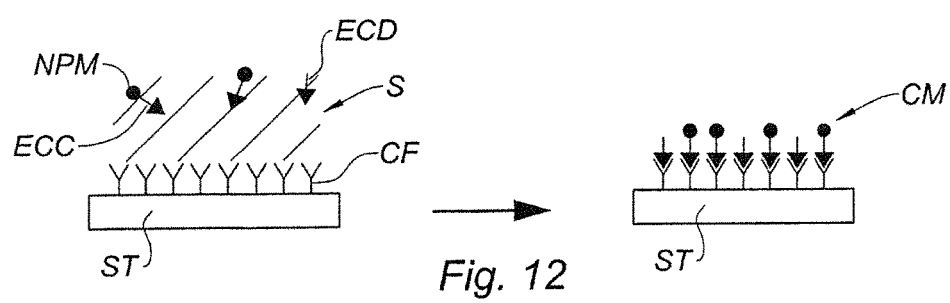

According to a fourth embodiment (FIG. 12), said functionalization layer is placed in contact with a solution S containing the chemical or biological species to be quantitatively determined, and also said competing chemical or biological species ECC, one of the two species (preferably the competing species) being labeled with metal nanoparticles or an absorbent label. Thus, a metallic or absorbent layer CM is obtained, the effective thickness and the effective index of which depend on the ratio between the concentration of said competing chemical or biological species and that of said chemical or biological species to be quantitatively determined. As in the other embodiments, the signal depends on this effective thickness and on this effective index.

The chemical or biological species may be, for example, antibodies, antigens, proteins, microorganisms, etc.

Instead of being metallic or absorbent, the label may be a scattering label. Indeed, it is known that the effect of scattering can be expressed via a refractive index which has an imaginary part.

The techniques for detection or quantitative determination described above also apply when the functionalization layer is deposited on a contrast-amplifying layer as described above. The functionalized layer and, where appropriate, the contrast-amplifying layer may be structured in spots, and the surface outside these spots may be passivated, as explained above.

The invention claimed is:

1. A process for observing a sample, comprising the steps:
   a) providing a sample support comprising a transparent substrate (ST) on which is deposited a coating comprising at least one layer, termed contrast-amplifying layer, having a complex refractive index with an imaginary part κ greater than or equal to 0.001;
   b) placing the sample to be observed on said coating comprising the contrast-amplifying layer;
   c) directing onto said sample, through said substrate, a spatially incoherent and not polarized light beam, focused so as to form an illumination cone having an aperture half-angle θ greater than or equal to 20°; and
   d) observing said sample through an objective and said substrate;
   said contrast-amplifying layer being proportioned so that said sample is observed with a higher contrast than in the absence of said support,
wherein a thickness of said contrast-amplifying layer is determined so as to optimize, for at least one illumination wavelength, the contrast integrated on said illumination cone with which would be observed a reference sample made up of a variation in thickness of said contrast-amplifying layer.

2. The process for observing a sample as claimed in claim 1, wherein said contrast-amplifying layer is metallic.

3. The process for observing a sample as claimed in claim 1, wherein the aperture half-angle of said illumination cone is selected from the group consisting of between 20° and 75°, between 30° and 70° and between 40° and 65°, the axis of said cone being perpendicular to said substrate.

4. The process for observing a sample as claimed in claim 1, wherein said objective is used both for illuminating and for observing said sample.

5. The process for observing a sample as claimed in claim 1, wherein step d) is carried out while the contrast-amplifying layer and said sample are immersed in water or in an aqueous solution.

6. The process for observing a sample as claimed in claim 1, wherein said contrast-amplifying layer has a thickness gradient which, at least one location is determined so as to optimize, for at least one illumination wavelength, the contrast integrated on said illumination cone with which would be observed a reference sample made up of a variation in thickness of said contrast-amplifying layer.

7. The process for observing a sample as claimed in claim 1, comprising a preliminary step of proportioning said contrast-amplifying layer, comprising:
   calculating an area representing the contrast with which said reference sample would be observed as a function of the thickness of said layer, normalized with respect to an illumination wavelength, and the aperture half-angle θ of the illumination beam;
   identifying a crest or thalweg of said area, having an orientation approximately parallel to the axis representing said aperture half-angle θ;
   identifying a value, or range of values, of thickness of said layer corresponding to said crest or thalweg;
   the thickness or a local thickness of said contrast-amplifying layer being chosen equal to the value, or within the value range, thus identified.

8. The process for observing a sample as claimed in claim 1, wherein said sample support has, above said contrast-amplifying layer, a functionalization layer capable of binding at least one chemical or biological species , the process also comprising a step of bringing said functionalization layer into contact with a solution of said chemical or biological species to be bound, as a result of which said chemical or biological species forms a layer above said functionalization layer, constituting the sample to be observed.

9. The process as claimed in claim 8, wherein said or at least one chemical or biological species is absorbent, having a complex refractive index with an imaginary part κ greater than or equal to 0.0001, or scattering.

10. The process as claimed in claim 8, wherein said functionalization layer is in the form of a plurality of spots capable of binding different chemical or biological species.

11. The process as claimed in claim 10, wherein said contrast layer is deposited only in positions corresponding to said spots.

12. The process as claimed in claim 10, wherein said support comprises, outside said spots, a passivation layer which prevents the binding of any chemical or biological species contained in said solution.

* * * * *

UNITED STATES PATENT AND TRADEMARK OFFICE
CERTIFICATE OF CORRECTION

PATENT NO. : 10,241,311 B2  
APPLICATION NO. : 14/417397  
DATED : March 26, 2019  
INVENTOR(S) : Ausserré et al.

Page 1 of 1

It is certified that error appears in the above-identified patent and that said Letters Patent is hereby corrected as shown below:

On the Title Page

Item (71) Applicants: "Marseilles (FR)" should read --Marseille (FR)--;  
Item (72) Inventors: "Marseilles (FR)", each occurrence, should read --Marseille (FR)--;  
Item (73) Assignees: "Marseilles (FR)" should read --Marseille (FR)--.

Signed and Sealed this  
Nineteenth Day of November, 2019

Andrei Iancu  
*Director of the United States Patent and Trademark Office*